United States Patent [19]

Unger et al.

[11] Patent Number: 5,469,854
[45] Date of Patent: Nov. 28, 1995

[54] METHODS OF PREPARING GAS-FILLED LIPOSOMES

[75] Inventors: Evan C. Unger; Thomas A. Fritz; Terry Matsunaga; VaradaRajan Ramaswami; David Yellowhair; Guanli Wu, all of Tucson, Ariz.

[73] Assignee: ImaR$_x$ Pharmaceutical Corp., Tucson, Ariz.

[21] Appl. No.: 76,239

[22] Filed: Jun. 11, 1993

Related U.S. Application Data

[63] Continuation-in-part of Ser. No. 717,084, Jun. 18, 1991, Pat. No. 5,228,446, and Ser. No. 716,899, Jun. 19, 1991, abandoned, each is a continuation-in-part of Ser. No. 569,828, Aug. 20, 1990, Pat. No. 5,088,499, which is a continuation-in-part of Ser. No. 455,707, Dec. 22, 1989, abandoned.

[51] Int. Cl.$^6$ ............................ A61B 8/00; A61K 9/66
[52] U.S. Cl. ............................ 128/662.02; 264/4.3
[58] Field of Search ............................ 128/662.02; 264/4.1, 264/4.3, 4.5; 424/9

[56] References Cited

U.S. PATENT DOCUMENTS

| | | | |
|---|---|---|---|
| B 14,229,360 | 11/1991 | Schneider et al. | 260/403 |
| 3,532,500 | 10/1970 | Priest et al. | 96/91 |
| 3,873,564 | 3/1975 | Schneider et al. | 260/309.6 |
| 4,089,801 | 5/1978 | Schneider | 252/316 |
| 4,162,282 | 7/1979 | Fulwyler et al. | 264/9 |
| 4,192,859 | 3/1980 | Mackaness et al. | 424/5 |
| 4,224,179 | 9/1980 | Schneider | 252/316 |

(List continued on next page.)

FOREIGN PATENT DOCUMENTS

| | | |
|---|---|---|
| 0107559 | 5/1984 | European Pat. Off. . |
| 0272091 | 6/1988 | European Pat. Off. . |
| 0324938 | 6/1988 | European Pat. Off. . |
| 0338971 | 10/1989 | European Pat. Off. . |
| 0361894 | 4/1990 | European Pat. Off. . |
| 0216730 | 1/1991 | European Pat. Off. . |
| 0458745A1 | 11/1991 | European Pat. Off. . |
| 0314764B1 | 9/1992 | European Pat. Off. . |
| 0554213A1 | 8/1993 | European Pat. Off. . |
| 63-60943 | 3/1988 | Japan . |
| 2193095A | 2/1988 | United Kingdom . |
| WO80/02365 | 11/1980 | WIPO . |
| WO82/01642 | 5/1982 | WIPO . |
| WO85/01161 | 3/1985 | WIPO . |
| WO86/00238 | 1/1986 | WIPO . |
| WO86/01103 | 2/1986 | WIPO . |
| WO89/05040 | 6/1989 | WIPO . |
| WO90/04943 | 5/1990 | WIPO . |
| WO91/00086 | 1/1991 | WIPO . |
| WO91/15244 | 10/1991 | WIPO . |
| WO92/10166 | 6/1992 | WIPO . |
| WO92/17212 | 10/1992 | WIPO . |
| WO93/05819 | 1/1993 | WIPO . |
| WO93/20802 | 3/1993 | WIPO . |
| WO93/06869 | 4/1993 | WIPO . |
| WO93/13809 | 7/1993 | WIPO . |

OTHER PUBLICATIONS

Nayar, R. et al "Generation of Large LUVs from Long-Chain Saturated PCs by Extrusion Technique", Biochimica & Biophysics Acta Elsevier Publ 986 (1989) 200–206.
Kost et al. Ultrasonic Modulated Drug Delivery Systems *Polymers in Medicine II* Plenum Press New York 387–396.
Brown et al. Transdermal Delivery of Drugs *Ann. Rev. Med.* 1988 39:221–229.
Gramiak et al., *Radiology*, "Detection of Intracardiac Blood Flow by Pulsed Echo–Ranging", pp. 415–418 (1971).
Feigenbaum et al., *Circulation*, "Identification of Ultrasound (List continued on next page.)

Primary Examiner—Francis Jaworski
Attorney, Agent, or Firm—Woodcock Washburn Kurtz Mackiewicz & Norris

[57] ABSTRACT

Methods of and apparatus for preparing gas-filled liposomes are described. Gas-filled liposomes prepared by these methods are particularly useful, for example, in ultrasonic imaging applications and in therapeutic drug delivery systems.

19 Claims, 10 Drawing Sheets

U.S. PATENT DOCUMENTS

| | | |
|---|---|---|
| 4,229,360 | 10/1980 | Schneider et al. ............... 260/403 |
| 4,276,885 | 7/1981 | Tickner et al. ................... 128/660 |
| 4,310,505 | 1/1982 | Baldeschwieler et al. .......... 424/1 |
| 4,310,506 | 1/1982 | Baldeschwieler ................. 424/1 |
| 4,315,514 | 2/1982 | Drewes et al. ................... 128/653 |
| 4,331,654 | 5/1982 | Morris ............................. 424/38 |
| 4,344,929 | 8/1982 | Bonsen et al. .................... 424/15 |
| 4,426,330 | 1/1984 | Sears ............................... 260/403 |
| 4,442,843 | 4/1984 | Rasor et al. ...................... 128/660 |
| 4,466,442 | 8/1984 | Hilmann et al. .................. 128/653 |
| 4,533,254 | 8/1985 | Cook et al. ....................... 366/176 |
| 4,534,899 | 8/1985 | Sears ............................... 260/403 |
| 4,544,545 | 10/1985 | Ryan et al. ....................... 424/1.1 |
| 4,569,836 | 2/1986 | Gordon . |
| 4,572,203 | 2/1986 | Feinstein .......................... 128/661 |
| 4,586,512 | 5/1986 | Do-huu et al. .................... 128/660 |
| 4,603,044 | 7/1986 | Geho et al. ....................... 424/9 |
| 4,620,546 | 11/1986 | Aida et al. ........................ 128/660 |
| 4,646,756 | 3/1987 | Watmough et al. ............... 128/804 |
| 4,657,756 | 4/1987 | Rasor et al. ...................... 424/9 |
| 4,658,828 | 4/1987 | Dory ................................ 128/660 |
| 4,675,310 | 6/1987 | Chapman et al. ................. 514/6 |
| 4,681,119 | 7/1987 | Rasor et al. ...................... 128/660 |
| 4,684,479 | 8/1987 | D'Arrigo .......................... 252/307 |
| 4,689,986 | 9/1987 | Carson et al. ..................... 73/19 |
| 4,718,433 | 1/1988 | Feinstein .......................... 128/660 |
| 4,728,575 | 3/1988 | Gamble et al. ................... 428/402.2 |
| 4,728,578 | 3/1988 | Higgins et al. ................... 428/662 |
| 4,737,323 | 4/1988 | Martin et al. ..................... 264/4.3 |
| 4,774,958 | 10/1988 | Feinstein .......................... 128/660.01 |
| 4,776,991 | 10/1988 | Farmer et al. .................... 264/4.3 |
| 4,781,871 | 11/1988 | West, III et al. .................. 264/4.3 |
| 4,790,891 | 12/1988 | Halliday et al. .................. 149/2 |
| 4,830,858 | 5/1989 | Payne et al. ...................... 424/450 |
| 4,844,882 | 7/1989 | Widder et al. .................... 424/9 |
| 4,863,717 | 9/1989 | Keana ............................... 424/9 |
| 4,865,836 | 9/1989 | Long, Jr. .......................... 424/5 |
| 4,877,561 | 10/1989 | Iga et al. ........................... 264/4.3 |
| 4,893,624 | 1/1990 | Lele ................................. 424/399 |
| 4,895,719 | 1/1990 | Radhakrishnan et al. ......... 424/45 |
| 4,898,734 | 2/1990 | Mathiowitz et al. .............. 424/426 |
| 4,900,540 | 2/1990 | Ryan et al. ....................... 424/9 |
| 4,921,706 | 5/1990 | Roberts et al. .................... 424/450 |
| 4,927,623 | 5/1990 | Long, Jr. .......................... 424/5 |
| 4,938,947 | 7/1990 | Nicolau et al. ................... 424/1.1 |
| 4,957,656 | 9/1990 | Cerny et al. ...................... 252/311 |
| 4,987,154 | 1/1991 | Long, Jr. .......................... 514/772 |
| 5,000,960 | 3/1991 | Wallach ............................ 424/450 |
| 5,008,050 | 4/1991 | Cullis et al. ...................... 264/4.3 |
| 5,013,556 | 5/1991 | Woodle et al. .................... 424/450 |
| 5,045,304 | 9/1991 | Schneider et al. ................ 424/9 |
| 5,049,388 | 9/1991 | Knight et al. ..................... 424/450 |
| 5,088,499 | 2/1992 | Unger ............................... 128/662.2 |
| 5,144,703 | 5/1992 | Wolf et al. ........................ 424/5 |
| 5,171,755 | 12/1992 | Kaufman .......................... 514/759 |
| 5,194,266 | 3/1993 | Abra et al. ........................ 424/450 |
| 5,195,520 | 3/1993 | Schlief et al. ..................... 128/660.02 |
| 5,198,225 | 3/1993 | Meybeck et al. ................. 424/450 |
| 5,213,804 | 5/1993 | Martin et al. ..................... 424/450 |
| 5,215,680 | 6/1993 | D'Arrigo .......................... 252/307 |
| 5,219,538 | 6/1993 | Henderson et al. ............... 428/402.2 |
| 5,271,928 | 12/1993 | Schneider et al. ................ 424/9 |
| 5,310,540 | 5/1994 | Giddey et al. .................... 424/9 |
| 5,316,771 | 5/1994 | Barenholtz et al. ............... 424/450 |

OTHER PUBLICATIONS

Echoes from the Left Ventricle by Use of Intracardiac Injections of Indocyanine Green", vol. XL1, pp. 615–621 (1970).

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol.* 3, 1978, 341–350.

Chapman et al., "Biomembrane Phase Transitions", *J. Biol. Chem.*, 1974, 249:2512–2521.

deGier et al., "Relations Between Liposomes and Biomembranes", *Annals of The New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli et al., "Incorporation of new amphiphilic perfluoroalkylated bipyridine platinum and palladium complexes into liposomes: stability and structure–incorporation relationships", *Biochimica et Biophysica Acta*, 1992, 1127:41–48.

Hug et al., "Liposomes for the transformation of eukaryotic cells", *Biochimica et Biophysica Acta*, 1991, 1097:1–17.

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination Chemistry of DNA Constituents", *J. Am. Chem. Soc.*, 1991, 113:9027–9045.

*Mammalian Cell Biotechnology: A Practical Approach*, M. Butler, 1991 (Oxford University Press, New York), pp. 57–70.

Marsh, Derek, *CRC Handbook of Lipid Bilayers* (CRC Press, Boca Raton, Fla. 1990) pp. 139–141.

Mathiowitz et al., "Photochemical Rupture of Microcapsules: A Model System", *Journal of Applied Polymer Science*, 1981, 26:809≡822.

Mathiowitz et al., "Polyanhydride Microspheres as Drug Carriers", *Journal of Applied Polymers Science*, 1988, 35:755–774.

May et al., "Cationic Liposomes Enable Bovine Herpesvirus Type 2 DNA to Infect Cells", *Acta virol.*, 1991, 35:107.

Mayhew et al., *Biochimica et Biophysica Acta*, 1984, 775:169–174.

Chiellini et al., *Polymers in Medicine II Biomedical and Pharmaceutical Applications*, (Plenum Press, New York and London) pp. 387–396.

Poznansky et al, "Biological Approaches to the Controlled Delivery of Drugs: A Critical Review", *Pharmacol. Rev.*, 1984, 36:277–336.

Sankaram et al., "Cholesterol–induced fluid–phase immiscibility in membranes", *Proc. Natl. Acad. Sci.*, 1991, 88:8686–8690.

Simons et al., "Antisense c–myb oligonucleotides inhibit intimal arterial smooth muscle cell accumulation in vivo", *Nature*, 1992, 359:67–70.

Szoka and Papahadjopoulos, "Procedure for preparation of liposomes with large internal aqueous space and high capture by reverse–phase evaporation", *Proc. Natl. Acad. Sci.*, 1978, 75:4194–4198.

Gregoriadis, ed., *Liposome Technology*, vol. I, pp. 1–18, 29–35, 51–65, 79–107 (CRC Press, Boca Raton, Fla. 1984).

Trubetskoy et al. "Cationic liposomes enhance targeted delivery and expression of exogenous DNA mediated by N–terminal modified poly(L–lysine)–antibody conjugate in mouse lung endothelial cells", *Biochimica et Biophysica Acta* 1992, 131:311–313.

Umemura et al., "Studies on Sonodynamic Cancer Therapy", *IEEE*, 1992, O–7803–0785, pp. 354–355.

Williams, "Human Gene Therapy: Searching for Better Vectors", *ASM News [American Society for Microbology]* 1992, 58:67–69.

Woodle et al., "Versatility in lipid compositions showing prolonged circulation with sterically stablized liposomes", *Biochimica et Biophysica Acta* 1992, 1105:193–200.

Sato et al., "Recent Aspects in the Use of Liposomes in Biotechnology and Medicine", *Prog. Lipid Res.* 1992, 4:345–372.

Zhou et al., "Targeted delivery of DNA by liposomes and polymers", *J. of Controlled Release* 1992, 19:269–274.

Cheng et al, "The Production and Evaluation of Contrast–Carrying Liposomes Made with an Automatic High–Pressure System", *Investigative Radiology* 1987, 22:47–55.

Crowe et al., "Preservation of Freeze–Dried Liposomes by Trehalose", *Archives of Biochemistry and Biophysics* 1985, 242:240–247.

Crowe et al., "Preservation of Structural and functional Activity in Lyophilized Sarcoplasmic Reticulum", *Archives of Biochemistry and Biophysics* 1983, 220:477–484.

Sinkula et al., "Rationale for Design of Biologically Reversible Drug Derivatives: Prodrugs", *J. Pharm. Sci.* 1975, 64:181–210.

Shiina et al., "Hyperthermiably Low–frequency Synthesized Ultrasound", *IEEE Engineering*, vol. 2, pp. 879–880 (abstract).

Hope et al., "Production of large unilamellar vesicles by a rapid extrusion procedure. Characterization of size distribution, trapped volume and ability to maintain a membrane potential", *Biochimica et Biophysica Acta* 1985, 812:55–65.

McAvoy et al., "Ultrasonics symposium Proceedings", *IEEE Engineering*, vol. 2, pp. 677–1248 (abstract).

Mayhem et al., "High–Pressure Continuous–flow System for Drug Entrapment in Liposomes", *Methods in Enzymology* 1987, 149:64–77.[0001]

Mayer et al., "Vesicles of variable sizes produced by a rapid extrusion procedure", *Biochimica et Biophysica Acta* 1986, 858:161–168.

Fitzpatrick et al. Metal Ion Catalyzed Decarboxylation: Kinetics and Mechanism fo the Oxidative Decarboxylation of Copper (II) Complexes of Aminomalonic Acid in Aqueous Solution *Inorganic Chem.* 1974 13:568–574.

Thanassi Aminomalonic Acid: Spontaneous Decarboxylationand reaction with 5–Deoxypyridoxal *Biochemistry* 1970 9:525 . 532.

Stelmasho et al. *Koordinatsionnaya Khimiya* 1977 3:524–527 (English Version).

Jain et al. *Introduction to Biological Membranes* Ch. 9 192–231 J. Wiley and Sons, N.Y. 1980.

Sigel H. Ed., *Metal Ions in Biological Systems: Antibiotics and Their Complexes* vol. 19 Marcell Dekker N.Y. 1985.

Nayar et al. Generation of Large Unilamellar Vesicles From Long–Chanin Saturated Phosphtidylcholines by Extrusion Technique Biochimica et Biophysica Acta 1989 986:200–206.

Hope et al. Generation of Multilamellar and Unilamellar Phospholipid Vesicles *Chem. Phys. of Lipids* 1986 40:89–107.

Mattrey et al. Perfluorochemicals as US Contrast Agents for Tumor–Imaging and Hepatosplenography: Preliminary Clinical Results *Radiology* 1987 163:339–343.

Mattrey et al. Perfluorocytlbromide: A Liver/Spleen–Specific and Tumor Imaging Ultrasound Contrast Material *Radiology* 1982 145:759–762.

Keller et al. Successful Left Ventricular Opacification Following Peripheral Venous Injection of Sonicated Contrast Agent *LV Contrast Echocardiography* 1987 114:570–575.

Feinstein et al. Two–Dimensional Contrast Echocardiography I *JACC* 1984 3:14–20.

Ten Cater et al. Two–Dimensional Contrast Echocardiography II *JACC* 1984 3:21–27.

Unger et al. Hepatic Metastases: Lipsomal Gd–DTPA–enhanced MR Imaging *Radiology* 1989 171:81–85.

Deamer et al. Permeability of Lipid Bilayers to Water and Ionic Solutes *Chem. Phys. Lipids* 1986 40:167–188.

Gutknecht et al. Diffusion of Carbon Dioxide Through Lipid Bilayer Membranes *Chemical Abstracts* 1977 87:34772g.

Scarpa et al. Cation Permeability of Liposomes as a Function of the Chmical Composition of the Lipid Bilyares *Biochimica et Biophysica Acta* 1971 241:789–797.

MacNaughton et al. Effects of Gaseous Anesthetics and Inert Gases on the Phase Transition in Smectic Mesophases of Dipalmitoyl Phosphatidylcholine *Biochim. et Biophy. Acta* 1980 597–193–198.

Tilcock et al. Liposomal Gd–DTPA *Radiology* 1989 171:77–80.

Mann et al. Formation of Iron Oxides in Unilamellar Vesciles *Journal of Colloid and Interface Science* 1988 122:326–335.

Anderson et al. Manganese (III) Complexes in Oxidative Decarboxylation of Acids *J. Am. Chem. COs.* 1970 92:2450–2460.

Muhlradt et al. Vitamin B6 Analogs *New Compounds* 1967 10:129–130.

Chapman D. Physiochemical Properties of Phopholipids and Lipid Water Systems *Liposome Technology* 1984 1:1–19.

Violante et al. Particulate Suspensions as Ultrasonic Contrast Agents for Liver and Spleen *Inv. Rad.* 1988 23:S294–S297.

Fritzsch et al. Preclinical and Clinical Results with an Ultrasonic Contrast Agent *Inv. Rad.* 1988 23:S302–S305.

Brochure, Experience, Sonicator, Heat Systems Ultrasonics, Inc. 1987.

Ostro M. Liposomes Marcel Dekker New York 1983 102–103.

Rose A. et al. The Condensed Chemical Dictionary Reinhold Publishing New York 1966 728 and 743.

Belykh A. G. Farmakol Toksikol (*MOSC*) 1981 44:322–326.

Vion–Dury et al. *J. Pharmacol. Exper. Ther.* 1989 250:1113–1118.

METHODS OF PREPARING GAS-FILLED LIPOSOMES

RELATED APPLICATION

This application is a continuation-in-part of application U.S. Ser. No. 717,084 now U.S. Pat. NO. 5,228,446 and U.S. Ser. No. 716,899, now abandoned, both of which were filed Jun. 18, 1991, which in turn are a continuation-in-part of U.S. Ser. No. 569,828, filed Aug. 20, 1990 and now U.S. Pat. No. 5,088,499, which in turn is a continuation-in-part of application U.S. Ser. No. 455,707, filed Dec. 22, 1989 and now abandoned. The disclosures of each of these patent applications are incorporated herein by reference in their entirety.

BACKGROUND OF THE INVENTION

1. Field of the Invention

This invention relates; to novel methods and apparatus for preparing gas-filled liposomes. Liposomes prepared by these methods are particularly useful, for example, in ultrasonic imaging applications and in therapeutic delivery systems.

2. Background of the Invention

A variety of imaging techniques have been used to detect and diagnose disease in animals and humans. X-rays represent one of the first techniques used for diagnostic imaging. The images obtained through this technique reflect the electron density of the object being imaged. Contrast agents such as barium or iodine have been used over the years to attenuate or block X-rays such that the contrast between various structures is increased. X-rays, however, are known to be somewhat dangerous, since the radiation employed in X-rays is ionizing, and the various deleterious effects of ionizing radiation are cumulative.

Another important imaging technique is magnetic resonance imaging (MRI). This technique, however, has various drawbacks such as expense and the fact that it cannot be conducted as a portable examination. In addition, MRI is not available at many medical centers.

Radionuclides, employed in nuclear medicine, provide a further imaging technique. In employing this technique, radionuclides such as technetium labelled compounds are injected into the patient, and images are obtained from gamma cameras. Nuclear medicine techniques, however, suffer from poor spatial resolution and expose the animal or patient to the deleterious effects of radiation. Furthermore, the handling and disposal of radionuclides is problematic.

Ultrasound is another diagnostic imaging technique which is unlike nuclear medicine and X-rays since it does not expose the patient to the harmful effects of ionizing radiation. Moreover, unlike magnetic resonance imaging, ultrasound is relatively inexpensive and can be conducted as a portable examination. In using the ultrasound technique, sound is transmitted into a patient or animal via a transducer. When the sound waves propagate through the body, they encounter interfaces from tissues and fluids. Depending on the acoustic properties of the tissues and fluids in the body, the ultrasound sound waves are partially or wholly reflected or absorbed. When sound waves are reflected by an interface they are detected by the receiver in the transducer and processed to form an image. The acoustic properties of the tissues and fluids within the body determine the contrast which appears in the resultant image.

Advances have been made in recent years in ultrasound technology. However, despite these various technological improvements, ultrasound is still an imperfect tool in a number of respects, particularly with regard to the imaging and detection of disease in the liver and spleen, kidneys, heart and vasculature, including measuring blood flow. The ability to detect and measure these regions depends on the difference in acoustic properties between tissues or fluids and the surrounding tissues or fluids. As a result, contrast agents have been sought which will increase the acoustic difference between tissues or fluids and the surrounding tissues or fluids in order to improve ultrasonic imaging and disease detection.

The principles underlying image formation in ultrasound have directed researchers to the pursuit of gaseous contrast agents. Changes in acoustic properties or acoustic impedance are most pronounced at interfaces of different substances with greatly differing density or acoustic impedance, particularly at the interface between solids, liquids and gases. When ultrasound sound waves encounter such interfaces, the changes in acoustic impedance result in a more intense reflection of sound waves and a more intense signal in the ultrasound image. An additional factor affecting the efficiency or reflection of sound is the elasticity of the reflecting interface. The greater the elasticity of this interface, the more efficient the reflection of sound. Substances such as gas bubbles present highly elastic interfaces. Thus, as a result of the foregoing principles, researchers have focused on the development of ultrasound contrast agents based on gas bubbles or gas containing bodies and on the development of efficient methods for their preparation.

Another area of significant research effort is in the area of targeted drug delivery. Targeted delivery means are particularly important where toxicity is an issue. Specific therapeutic delivery methods potentially serve to minimize toxic side effects, lower the required dosage amounts, and decrease costs for the patient.

The methods and materials in the prior art for introduction of genetic materials, for example, to living cells is limited and ineffective. To date several different mechanisms have been developed to deliver genetic material to living cells. These mechanisms include techniques such as calcium phosphate precipitation and electroporation, and carriers such as cationic polymers and aqueous-filled liposomes. These methods have all been relatively ineffective in vivo and only of limited use for cell culture transfection. None of these methods potentiate local release, delivery and integration of genetic material to the target cell.

Better means of delivery for therapeutics such as genetic materials are needed to treat a wide variety of human and animal diseases. Great strides have been made in characterizing genetic diseases and in understanding protein transcription but relatively little progress has been made in delivering genetic material to cells for treatment of human and animal disease.

A principal difficulty has been to deliver the genetic material from the extracellular space to the intracellular space or even to effectively localize genetic material at the surface of selected cell membranes. A variety of techniques have been tried in vivo but without great success. For example, viruses such as adenoviruses and retroviruses have been used as vectors to transfer genetic material to cells. Whole virus has been used but the amount of genetic material that can be placed inside of the viral capsule is limited and there is concern about possible dangerous interactions that might be caused by live virus. The essential components of the viral capsule may be isolated and used to carry genetic material to selected cells. In vivo, however, not only must the delivery vehicle recognize certain cells but it also must be delivered to these cells. Despite extensive work on viral vectors, it has been difficult to develop a successfully targeted viral mediated vector for delivery of genetic material in vivo.

Conventional, liquid-containing liposomes have been used to deliver genetic material to cells in cell culture but have mainly been ineffective in vivo for cellular delivery of genetic material. For example, cationic liposome transfection techniques have not worked effectively in vivo. More effective means are needed to improve the cellular delivery of therapeutics such as genetic material.

The present invention is directed to addressing the foregoing, as well as other important needs in the area of contrast agents for ultrasonic imaging and vehicles for the effective targeted delivery of therapeutics.

SUMMARY OF THE INVENTION

The present invention provides methods and apparatus for preparing gas-filled liposomes suitable for use as contrast agents for ultrasonic imaging or as drug delivery agents. The methods of the present invention provide the advantages, for example, of simplicity and potential cost savings during manufacturing of gas-filled liposomes.

Preferred methods for preparing the gas-filled liposomes comprise shaking an aqueous solution comprising a lipid in the presence of a gas, at a temperature below the gel state to liquid crystalline state phase transition temperature of the lipid.

Unexpectedly, the gas-filled liposomes prepared in accordance with the methods of the present invention possess a number of surprising yet highly beneficial characteristics. For example, gas-filled liposomes are advantageous due to their biocompatibility and the ease with which lipophilic compounds can be made to cross cell membranes after the liposomes are ruptured. The liposomes of the invention also exhibit intense echogenicity on ultrasound, are highly stable to pressure, and/or generally possess a long storage life, either when stored dry or suspended in a liquid medium. The echogenicity of the liposomes is of importance to the diagnostic and therapeutic applications of the liposomes made according to the invention. The gas-filled liposomes also have the advantages, for example, of stable particle size, low toxicity and compliant membranes. It is believed that the flexible membranes of tile gas-filled liposomes may be useful in aiding the accumulation or targeting of these liposomes to tissues such as tumors.

The gas-filled liposomes made according to the present invention thus have superior characteristics for ultrasound contrast imaging. When inside an aqueous or tissue media, the gas-filled liposome creates an interface for the enhanced absorption of sound. The gas-filled liposomes are therefore useful in imaging a patient generally, and/or in diagnosing the presence of diseased tissue in a patient as well as in tissue heating and the facilitation of drug release or activation.

In addition to ultrasound, the gas-filled liposomes made according to the present invention may be used, for example, for magnetic imaging and as MRI contrast agents. For example, the gas-filled liposomes may contain paramagnetic gases, such as atmospheric air, which contains traces of oxygen 17, or paramagnetic ions such as $Mn^{+2}$, $Gd^{+2}$, $Fe^{+3}$, and may thus be used as susceptibility contrast agents for magnetic resonance imaging. Additionally, for example, the gas-filled liposomes made according to the present invention may contain radioopaque metal ions, such as iodine, barium, bromine, or tungsten, for use as x-ray contrast agents.

The gas-filled liposomes are also particularly useful as drug carriers. Unlike liposomes of the prior art that have a liquid interior suitable only for encapsulating drugs that are water soluble, the gas-filled liposomes made according to the present invention are particularly useful for encapsulating lipophilic drugs. Furthermore, lipophilic derivatives of drugs may be incorporated into the lipid layer readily, such as alkylated derivatives of metallocene dihalides. Kuo et al., *J. Am. Chem. Soc.* 1991 113, 9027–9045.

DETAILED DESCRIPTION OF THE INVENTION

Figure 1:
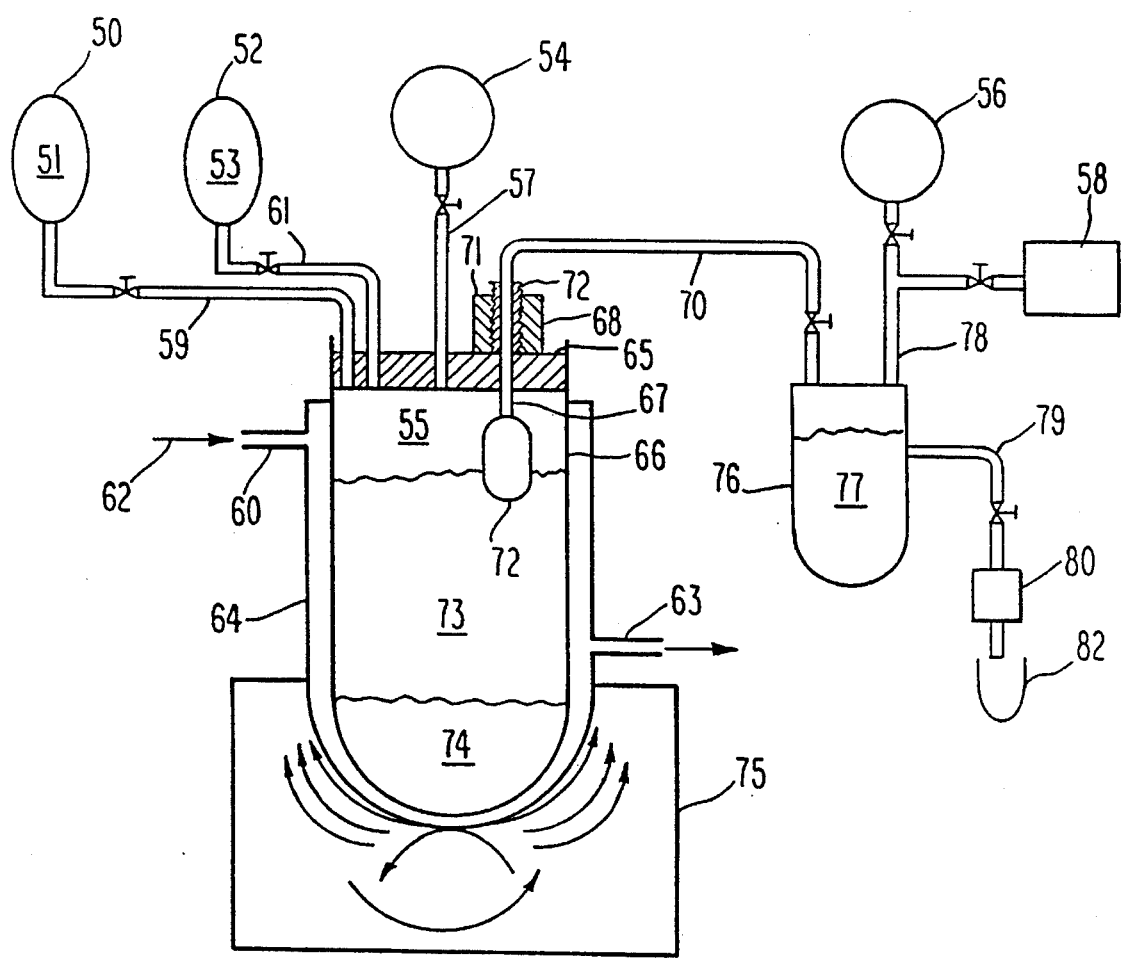
FIG. 1 is a view, partially schematic, of a preferred apparatus according to the present invention for preparing the gas-filled liposome microspheres of the present invention.

The present invention is directed to methods and apparatus for preparing gas-filled liposomes. Unlike the methods of the prior art which are directed to the formation of liposomes with an aqueous solution filling the interior, the methods of the present invention are directed to the preparation of liposomes which comprise interior gas.

Preferred methods for preparing the gas-filled liposomes comprise shaking an aqueous solution comprising a lipid in the presence of a gas at a temperature below the gel state to liquid crystalline state phase transition temperature of the lipid. The present invention also provides a method for preparing gas-filled liposomes comprising shaking an aqueous solution comprising a lipid in the presence of a gas, and separating the resulting gas-filled liposomes for diagnostic or therapeutic use. Liposomes prepared by the foregoing methods are referred to herein as gas-filled liposomes prepared by a gel state shaking gas installation method.

Conventional, aqueous-filled liposomes are routinely formed at a temperature above the phase transition temperature of the lipid, since they are more flexible and thus useful in biological systems in the liquid crystalline state. See, for example, Szoka and Papahadjopoulos, *Proc. Natl. Acad. Sci.* 1978 75, 4194–4198. In contrast, the liposomes made according to preferred embodiments of the methods of the present invention are gas-filled, which imparts greater flexibility since gas is more compressible and compliant than an aqueous solution. Thus, the gas-filled liposomes may be utilized in biological systems when formed at a temperature below the phase transition temperature of the lipid, even though the gel phase is more rigid.

The methods of the present invention provide for shaking an aqueous solution comprising a lipid in the presence of a gas. Shaking, as used herein, is defined as a motion that agitates an aqueous solution such that gas is introduced from the local ambient environment into the aqueous solution. Any type of motion that agitates the aqueous solution and results in the introduction of gas may be used for the shaking. The shaking must be of sufficient force to allow the formation of foam after a period of time. Preferably, the shaking is of sufficient force such that foam is formed within a short period of time, such as 30 minutes, and preferably within 20 minutes, and more preferably, within 10 minutes. The shaking may be by swirling (such as by vortexing), side-to-side, or up and down motion. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, a shaker table such as a VWR Scientific (Cerritos, Calif.) shaker table and a mechanical paint mixer, as well as other known machines. Another means for producing shaking includes the action of gas emitted under high velocity or pressure. It will also be understood that preferably, with a larger volume of aqueous solution, the total amount of force will be correspondingly increased. Vigorous shaking is defined as at least about 60 shaking motions per minute, and is preferred. Vortexing at least 1000 revolutions per minute, an example of vigorous shaking, is more preferred. Vortexing at 1800 revolutions per minute is most preferred.

The formation of gas-filled liposomes upon shaking can be detected by the presence of a foam on the top of the aqueous solution. This is coupled with a decrease in the volume of the aqueous solution upon the formation of foam. Preferably, the final volume of the foam is at least about two times the initial volume of the aqueous lipid solution; more preferably, the final volume of the foam is at least about three times the initial volume of the aqueous solution; even more preferably, the final volume of the foam is at least about four times the initial volume of the aqueous solution; and most preferably, all of the aqueous lipid solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gas-filled liposomes becomes sufficiently thick so that it no longer clings to the side walls as it is swirled. At this time, the foam may cause the solution containing the gas-filled liposomes to raise to a level of 30 to 35 ml.

The concentration of lipid required to form a preferred foam level will vary depending upon the type of lipid used, and may be readily determined by one skilled in the art, once armed with the present disclosure. For example, in preferred embodiments, the concentration of 1,2-dipalimitoylphosphatidylcholine (DPPC) used to form gas-filled liposomes according to the methods of the present invention is about 20 mg/ml to about 30 mg/ml saline solution. The concentration of distearoylphosphatidylcholine (DSPC) used in preferred embodiments is about 5 mg/ml to about 10 mg/ml saline solution.

Specifically, DPPC in a concentration of 20 mg/ml to 30 mg/ml, upon shaking, yields a total suspension and entrapped gas volume four times greater than the suspension volume alone. DSPC in a concentration of 10 mg/ml, upon shaking, yields a total volume completely devoid of any liquid suspension volume and contains entirely foam.

It will be understood by one skilled in the art, once armed with the present disclosure, that the lipids or liposomes may be manipulated prior and subsequent to being subjected to the methods of the present invention. For example, the lipid may be hydrated and then lyophilized, processed through freeze and thaw cycles, or simply hydrated. In preferred embodiments, the lipid is hydrated and then lyophilized, or hydrated, then processed through freeze and thaw cycles and then lyophilized, prior to the formation of gas-filled liposomes. In a most preferred embodiment, the lipid is hydrated and shaken, followed by at least one cycle of freezing in liquid nitrogen and thawing, and then followed by lyophilization. Advantages to these treatments prior to the final formation of gas-filled liposomes include the transformation of the lipid to a solid form having a higher surface area, thus permitting better solubilization upon hydration and subsequently a higher yield of gas-filled liposomes.

According to the methods of preferred embodiments of the present invention, the presence of gas is provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container.

The preferred methods of the invention are preferably carried out at a temperature below the gel state to liquid crystalline state phase transition temperature of the lipid employed. By "gel state to liquid crystalline state phase transition temperature", it is meant the temperature at which a lipid bilayer will convert from a gel state to a liquid crystalline state. See, for example, Chapman et al., *J. Biol. Chem.* 1974 249, 2512–2521. The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984) and Derek Marsh, *CRC Handbook of Lipid Bilayers* (CRC Press, Boca Raton, Fla. 1990), at p. 139. See also Table I, below. Where the gel state to liquid crystalline state phase transition temperature of the lipid employed is higher than room temperature, the temperature of the container may be regulated, for example, by providing a cooling mechanism to cool the container holding the lipid solution.

TABLE I

Saturated Diacyl-sn-Glycero-3-Phosphocholines
Main Chain Gel State to Liquid Crystalline State
Phase Transition Temperatures

| # Carbons in Acyl Chains | Liquid Crystalline Phase Transition Temperature (°C.) |
| --- | --- |
| 1,2-(12:0) | −1.0 |
| 1,2-(13:0) | 13.7 |
| 1,2-(14:0) | 23.5 |

TABLE I-continued

Saturated Diacyl-sn-Glycero-3-Phosphocholines
Main Chain Gel State to Liquid Crystalline State
Phase Transition Temperatures

| # Carbons in Acyl Chains | Liquid Crystalline Phase Transition Temperature (°C.) |
|---|---|
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

Conventional, aqueous-filled liposomes are routinely formed at a temperature above the gel to liquid crystalline phase transition temperature of the lipid, since they are more flexible and thus useful in biological systems in the liquid crystalline state. See, for example, Szoka and Papahadjopoulos, *Proc. Natl. Acad. Sci.* 1978 75, 4194–4198. In contrast, the liposomes made according to preferred embodiments of the methods of the present invention are gas-filled, which imparts greater flexibility since gas is more compressible and compliant than an aqueous solution. Thus, the gas-filled liposomes may be utilized in biological systems when formed at a temperature below the phase transition temperature of the lipid, even though the gel phase is more rigid.

A preferred apparatus for producing the gas-filled liposomes using a gel state shaking gas installation process is shown in FIG. 1. A mixture of lipid and aqueous media is vigorously agitated in the process of gas installation to produce gas-filled liposomes, either by batch or by continuous feed. Referring to FIG. 1, dried lipids 51 from a lipid supply vessel 50 are added via conduit 59 to a mixing vessel 66 in either a continuous flow or as intermittent boluses. If a batch process is utilized, the mixing vessel 66 may comprise a relatively small container such as a syringe, test tube, bottle or round bottom flask, or a large container. If a continuous feed process is utilized, the mixing vessel is preferably a large container, such as a vat.

Where the gas-filled liposomes contain a therapeutic compound, the therapeutic compound may be added, for example, in a manner similar to the addition of the lipid described above before the gas installation process. Alternatively, the therapeutic compound may be added after the gas installation process when the liposomes are coated on the outside with the therapeutic compound.

In addition to the lipids 51, an aqueous media 53, such as a saline solution, from an aqueous media supply vessel 52, is also added to the vessel 66 via conduit 61. The lipids 51 and the aqueous media 53 combine to form an aqueous lipid solution 74. Alternatively, the dried lipids 51 could be hydrated prior to being introduced into the mixing vessel 66 so that lipids are introduced in an aqueous solution. In the preferred embodiment of the method for making liposomes, the initial charge of solution 74 is such that the solution occupies only a portion of the capacity of the mixing vessel 66. Moreover, in a continuous process, the rates at which the aqueous lipid solution 74 is added and gas-filled liposomes produced are removed is controlled to ensure that the volume of lipid solution 74 does not exceed a predetermined percentage of the mixing vessel 66 capacity.

The shaking may be accomplished by introducing a high velocity jet of a pressurized gas directly into the aqueous lipid solution 74. Alternatively, the shaking may be accomplished by mechanically, shaking the aqueous solution, either manually or by machine. Such mechanical shaking may be effected by shaking the mixing vessel 66 or by shaking the aqueous solution 74 directly without shaking the mixing vessel itself. As shown in FIG. 1, in the preferred embodiment, a mechanical shaker 75, is connected to the mixing vessel 66. The shaking should be of sufficient intensity so that, after a period of time, a foam 73 comprised of gas-filled liposomes is formed on the top of the aqueous solution 74, as shown in FIG. 1. The detection of the formation of the foam 73 may be used as a means for controlling the duration of the shaking; that is, rather than shaking for a predetermined period of time, the shaking may be continued until a predetermined volume of foam has been produced.

In a preferred embodiment of the apparatus for making gas-filled liposomes in which the lipid employed has a gel to liquid crystalline phase transition temperature below room temperature, a means for cooling the aqueous lipid solution 74 is provided. In the embodiment shown in FIG. 1, cooling is accomplished by means of a jacket 64 disposed around the mixing vessel 66 so as to form an annular passage surrounding the vessel. As shown in FIG. 1, a cooling fluid 63 is forced to flow through this annular passage by means of jacket inlet and outlet ports 62 and 63, respectively. By regulating the temperature and flow rate of the cooling fluid 62, the temperature of the aqueous lipid solution 74 can be maintained at the desired temperature.

As shown in FIG. 1, a gas 55, which may be air or another gas, such as nitrogen or argon, is introduced into the mixing vessel 66 along with the aqueous solution 74. Air may be introduced by utilizing an unsealed mixing vessel so that the aqueous solution is continuously exposed to environmental air. In a batch process, a fixed charge of local ambient air may be introduced by sealing the mixing vessel 66. If a gas heavier than air is used, the container need not be sealed. However, introduction of gases that are not heavier than air will require that the mixing vessel be sealed, for example by use of a lid 65, as shown in FIG. 1. Whether the gas 55 is air or another gas, it may be pressurized in the mixing vessel 66, for example, by connecting the mixing vessel to a pressurized gas supply tank 54 via a conduit 57, as shown in FIG. 1.

After the shaking is completed, the gas-filled liposome containing foam 73 may be extracted from the mixing vessel 66. Extraction may be accomplished by inserting the needle 102 of a syringe 100, shown in FIG. 2, into the foam 73 and drawing a predetermined amount of foam into the barrel 104 by withdrawing the plunger 106. As discussed further below, the location at which the end of the needle 102 is placed in the foam 73 may be used to control the size of the gas-filled liposomes extracted.

Alternatively, extraction may be accomplished by inserting an extraction tube 67 into the mixing vessel 66, as shown in FIG. 1. If the mixing vessel 66 is pressurized, as previously discussed, the pressure of the gas 55 may be used to force the gas-filled liposomes 77 from the mixing vessel 66 to an extraction vessel 76 via conduit 70. In the event that the mixing vessel 66 is not pressurized, the extraction vessel 76 may be connected to a vacuum source 58, such as a vacuum pump, via conduit 78, that creates sufficient negative pressure to suck the foam 73 into the extraction vessel 76, as shown in FIG. 1. From the extraction vessel 76, the gas-filled liposomes 77 are introduced into vials 82 in which they may be shipped to the ultimate user. A source of pressurized gas 56 may be connected to the extraction vessel 76 as aid to ejecting the gas-filled liposomes. Since negative pressure may result in increasing the size of the gas-filled liposomes, positive pressure is preferred for removing the gas-filled liposomes.

Figure 4:
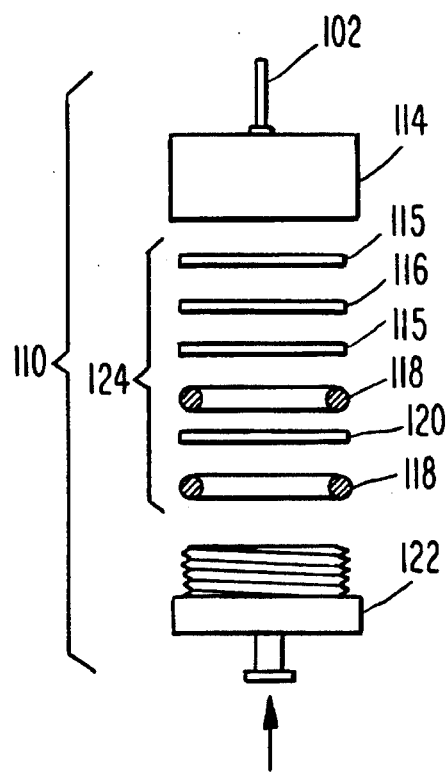
FIG. 4 is an exploded view of a portion of the apparatus of FIG. 3.
Figure 5A:
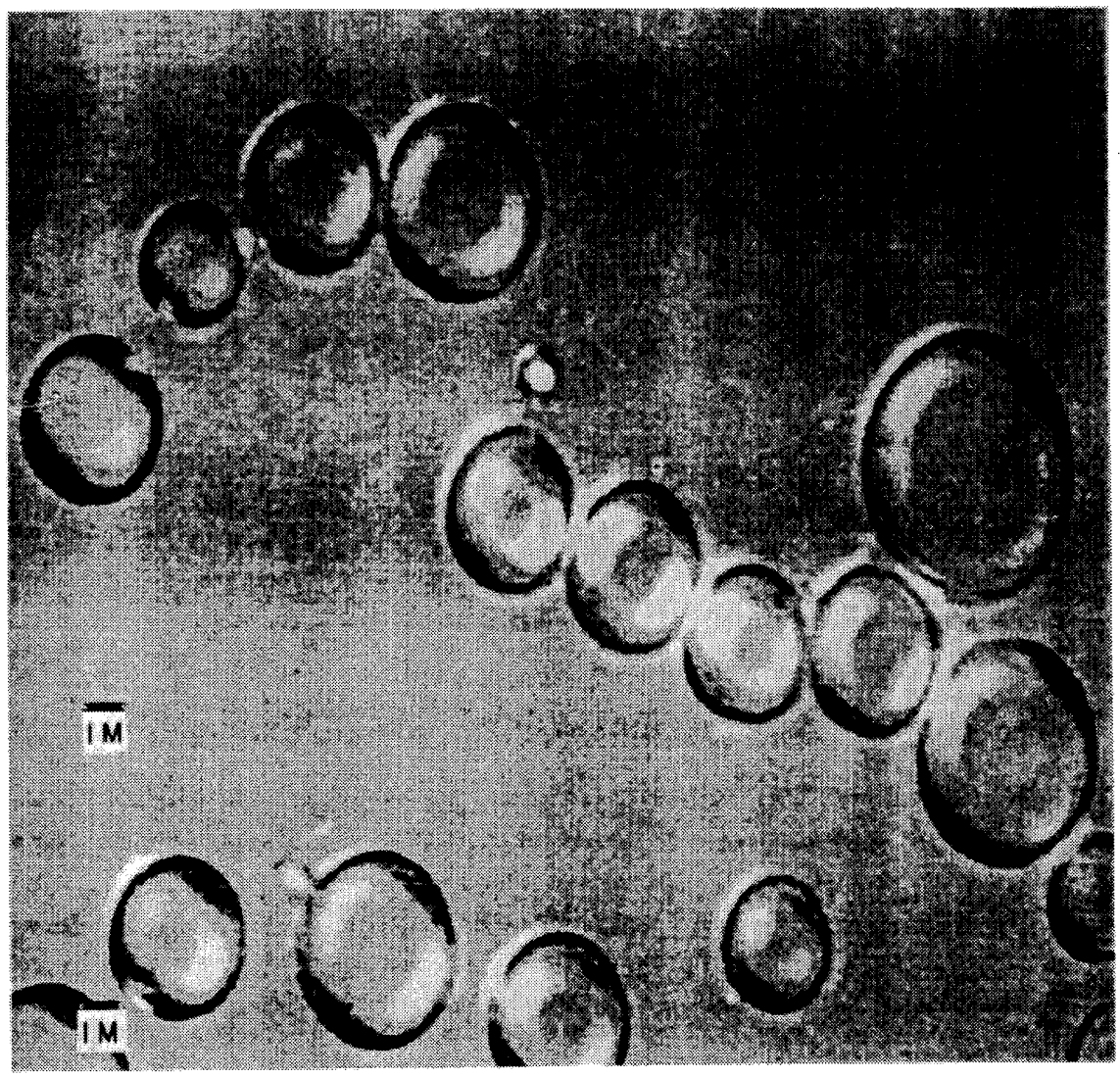
FIG. 5 is a micrograph which shows the sizes of gas-filled liposomes of the invention before (A) and after (B) filtration.
Figure 5B:
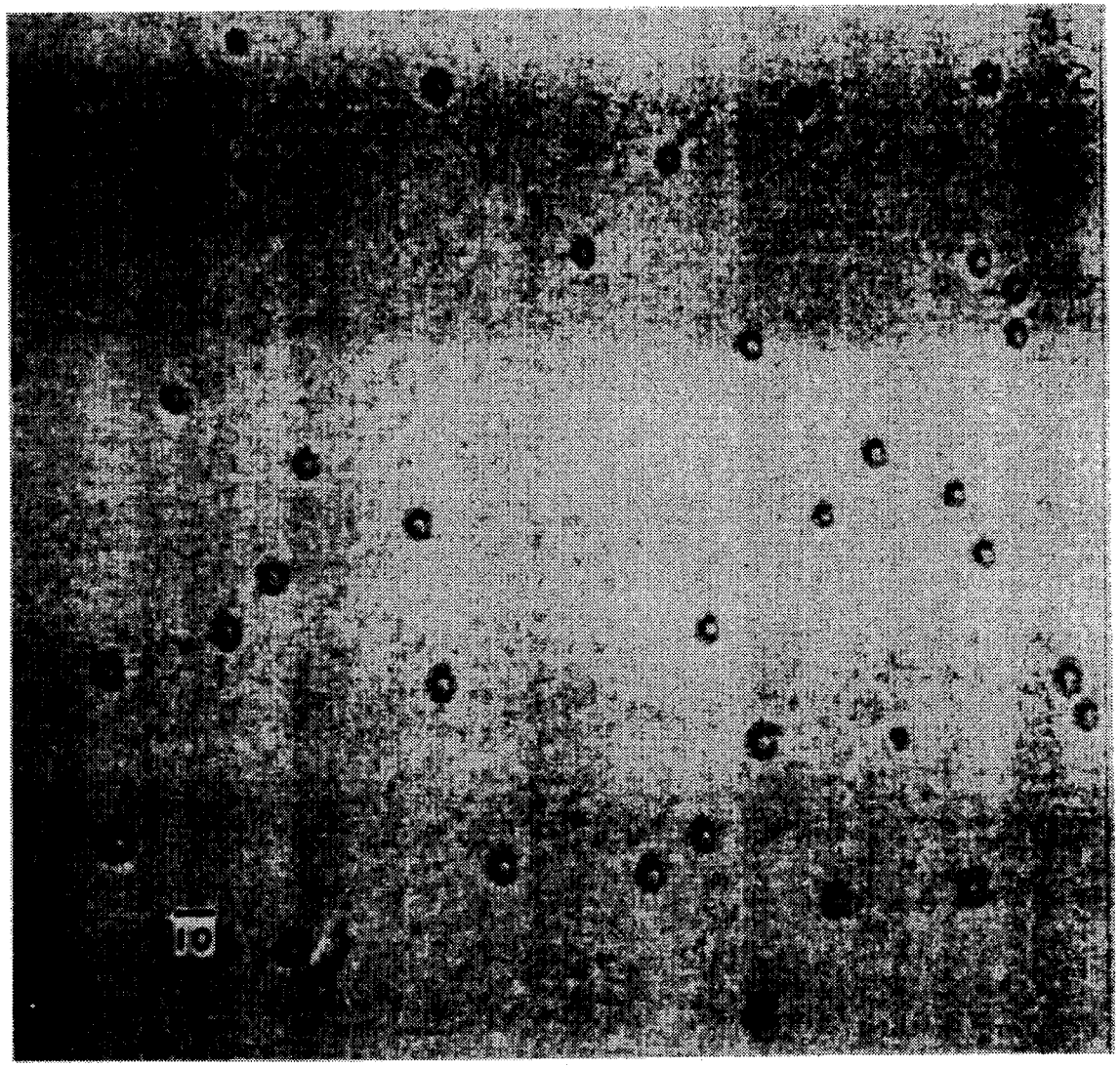
Figure 6A:
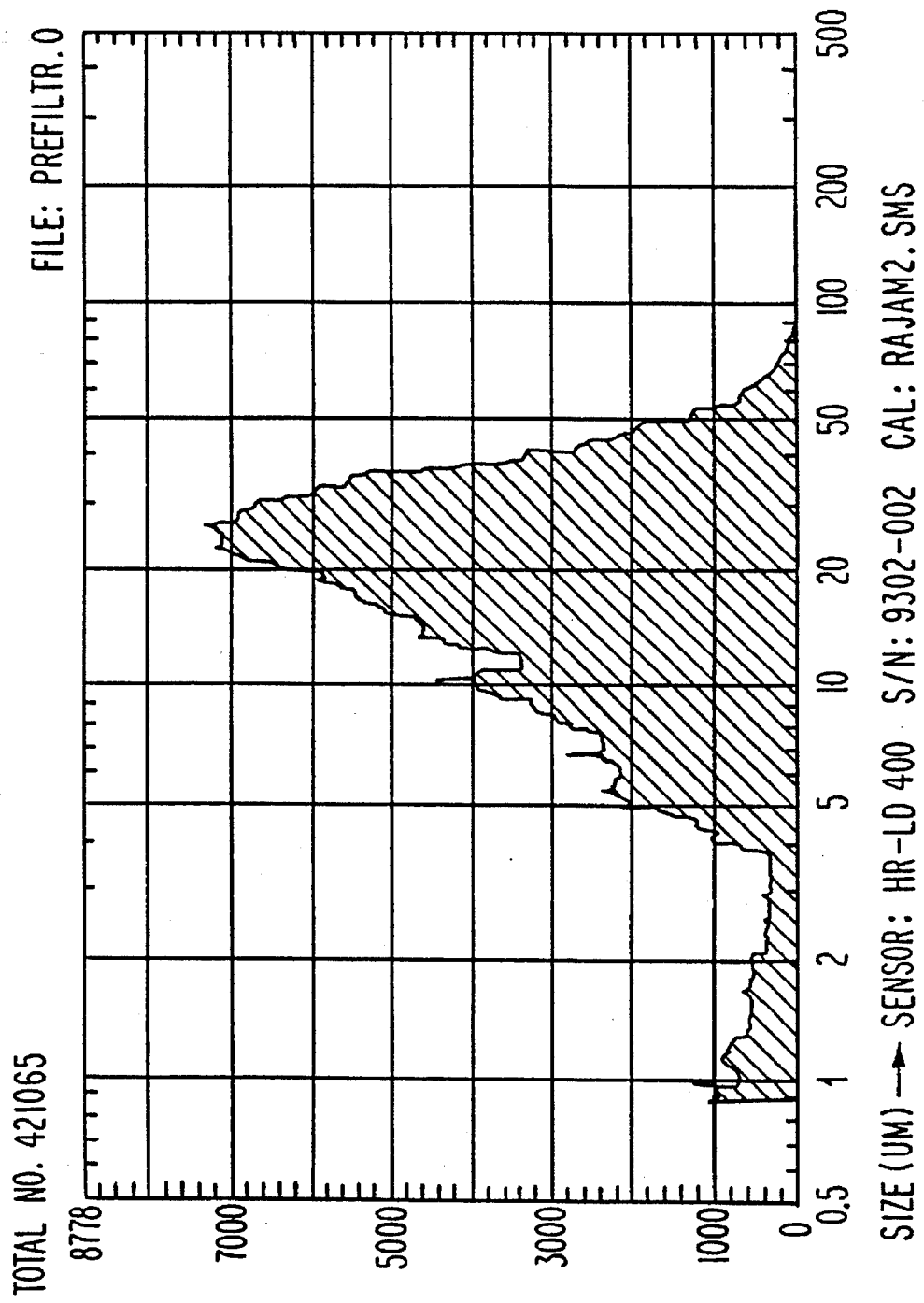
FIG. 6 graphically depicts the size distribution of gas-filled liposomes of the invention before (A) and after (B) filtration.
Figure 6B:
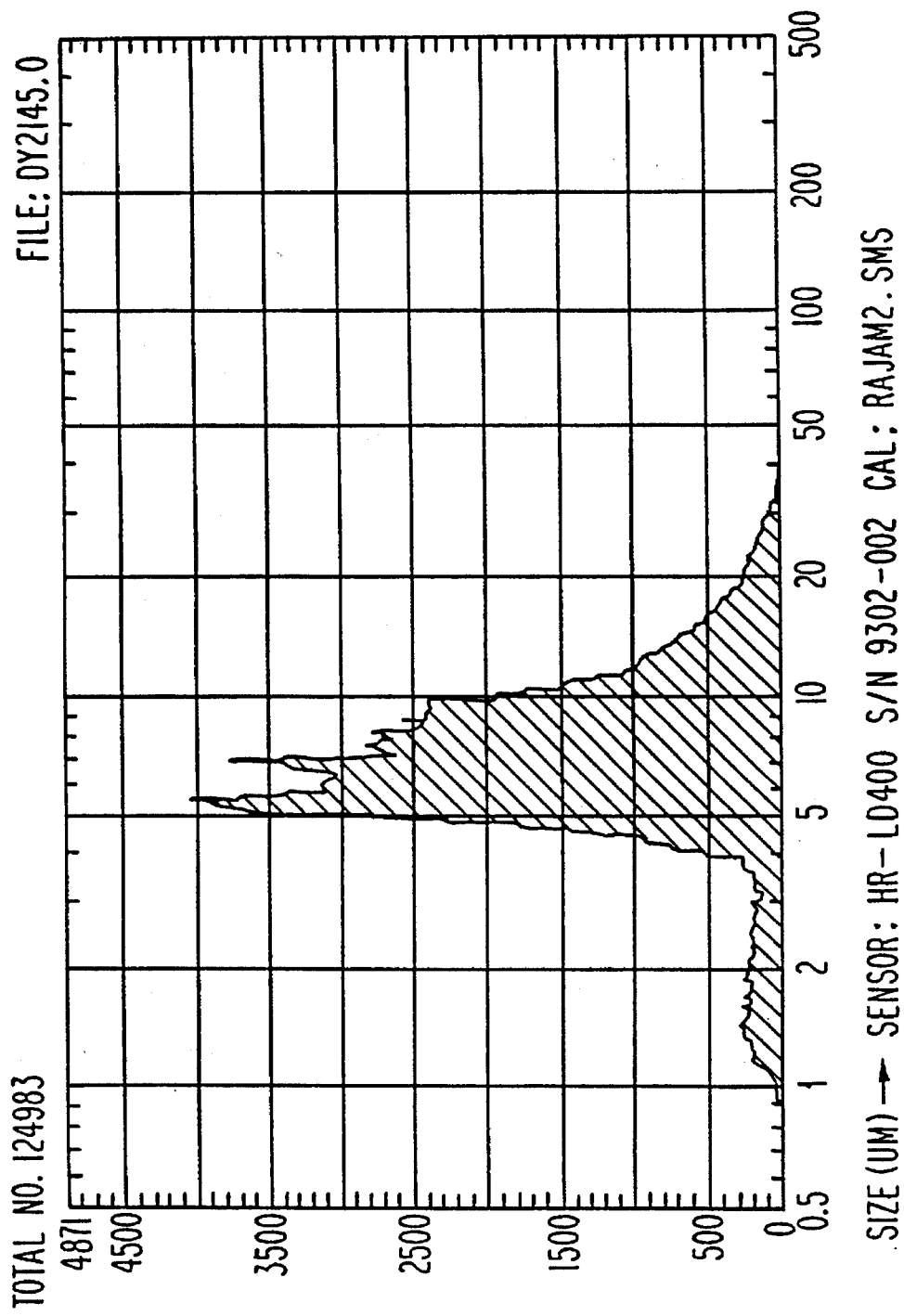

Filtration is preferably carried out in order to obtain gas-filled liposomes of a substantially uniform size. In certain preferred embodiments, the filtration assembly contains more than one filter, and preferably, the filters are not immediately adjacent to each other, as illustrated in FIG. 4. Before filtration, the gas-filled liposomes range in size from about 1 micron to greater than 60 microns (FIGS. 5A and 6A). After filtration through a single filter, the gas-filled liposomes are generally less than 10 microns but particles as large as 25 microns in size remain. After filtration through two filters (10 micron followed by 8 micron filter), almost all of the liposomes are less than 10 microns, and most are 5 to 7 microns (FIGS. 5B and 6B).

As shown in FIG. 1, filtering may be accomplished by incorporating a filter element 72 directly onto the end of the extraction tube 67 so that only gas-filled liposomes below a pre-determined size are extracted from the mixing vessel 66. Alternatively, or in addition to the extraction tube filter 72, gas-filled 2[liposome sizing may be accomplished by means of a filter 80 incorporated into the conduit 79 that directs the gas-filled liposomes 77 from the extraction vessel 76 to the vials 82, as shown in FIG. 1. The filter 80 may contain a cascade filter assembly 124, such as that shown in FIG. 4. The cascade filter assembly 124 shown in FIG. 4 comprises two successive filters 116 and 120, with filter 120 being disposed upstream of filter 116. In a preferred embodiment, the upstream filter 120 is a "NUCLEPORE" 10 µm filter and the downstream filter 116 is a "NUCLEPORE" 8 µm filter. Two 0.15 mm metallic mesh discs 115 are preferably installed on either side of the filter 116. In a preferred embodiment, the filters 116 and 120 are spaced apart a minimum of 150 µm by means of a Teflon™ O-ring, 118.

In addition to filtering, sizing may also be accomplished by taking advantage of the dependence of gas-filled liposome buoyancy on size. The gas-filled liposomes have appreciably lower density than water and hence will float to the top of the mixing vessel 66. Since the largest liposomes have the lowest density, they will float most quickly to the top. The smallest liposomes will generally be last to rise to the top and the non gas-filled lipid portion will sink to the bottom. This phenomenon may be advantageously used to size the gas-filled liposomes by removing them from the mixing vessel 66 via a differential flotation process. Thus, the setting of the vertical location of the extraction tube 67 within the mixing vessel 66 may control the size of the gas-filled liposomes extracted; the higher the tube, the larger the gas-filled liposomes extracted. Moreover, by periodically or continuously adjusting the vertical location of the extraction tube 67 within the mixing vessel 66, the size of the gas-filled liposomes extracted may be controlled on an on-going basis. Such extraction may be facilitated by incorporating a device 68, which may be a threaded collar 71 mating with a threaded sleeve 72 attached to the extraction tube 67, that allows the vertical location of the extraction tube 66 within the extraction vessel 66 to be accurately adjusted.

The gel state shaking gas installation process itself may also be used to improve sizing of the gas-filled lipid based microspheres. In general, the greater the intensity of the shaking energy, the smaller the size of the resulting gas-filled liposomes.

Figure 2:
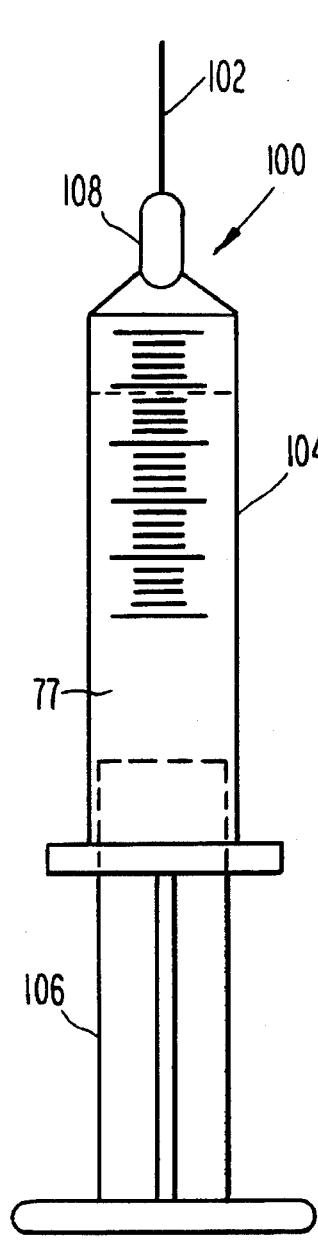
FIG. 2 shows a preferred apparatus for filtering and/or dispensing therapeutic containing gas-filled liposome microspheres of the present invention.

The current invention also includes novel methods for preparing drug-containing gas-filled liposomes to be dispensed to the ultimate user. Once gas-filled liposomes are formed, they can not be sterilized by heating at a temperature that would cause rupture. Therefore, it is desirable to form the gas-filled liposomes from sterile ingredients and to perform as little subsequent manipulation as possible to avoid the danger of contamination. According to the current invention, this may be accomplished, for example, by sterilizing the mixing vessel containing the lipid and aqueous solution before shaking and dispensing the gas-filled liposomes 77 from the mixing vessel 66, via the extraction vessel 76, directly into the barrel 104 of a sterile syringe 100, shown in FIG. 2, without further processing or handling; that is, without subsequent sterilization. The syringe 100, charged with gas-filled liposomes 77 and suitably packaged, may then be dispensed to the ultimate user. Thereafter, no further manipulation of the product is required in order to administer the gas-filled liposomes to the patient, other than removing the syringe from its packaging and removing a protector (not shown) from the syringe needle 102 and inserting the needle into the body of the patient, or into a catheter. Moreover, the pressure generated when the syringe plunger 106 is pressed into the barrel 104 will cause the largest gas-filled liposomes to collapse, thereby achieving a degree of sizing without filtration.

Where it is desired to filter the gas-filled liposomes at the point of use, for example because they are removed from the extraction vessel 76 without filtration or because further filtration is desired, the syringe 100 may be fitted with its own filter 108, as shown in FIG. 2. This results in the gas-filled liposomes being sized by causing them to be extruded through the filter 108 by the action of the plunger 106 when the gas-filled liposomes are injected. Thus, the gas-filled liposomes may be sized and injected into a patient in one step.

Figure 3:
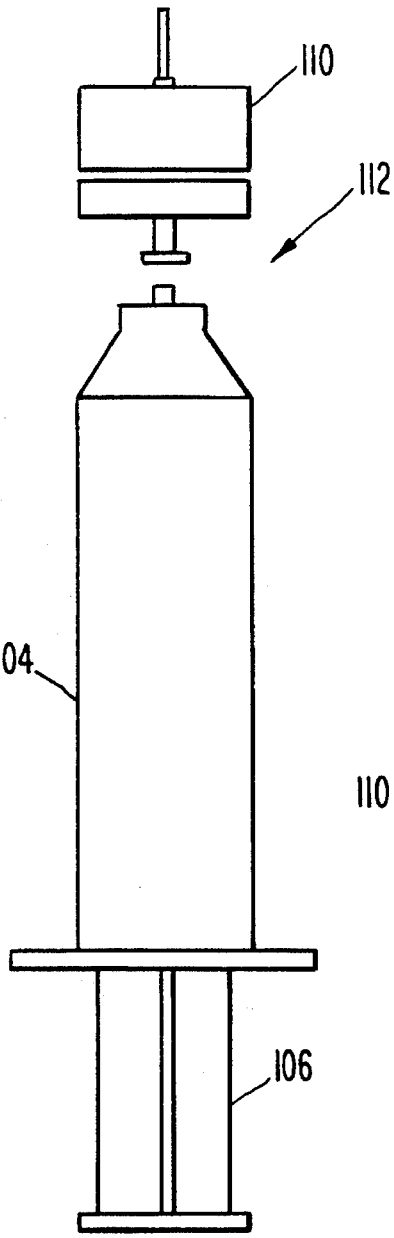
FIG. 3 shows a preferred apparatus for filtering and/or dispensing therapeutic containing gas-filled liposome microspheres of the present invention.

As shown in FIG. 3, a cascade filter housing 110 may be fitted directly onto a syringe 112, thereby allowing cascade filtration at the point of use. As shown in FIG. 4, the filter housing 110 is comprised of a cascade filter assembly 124, previously discussed, incorporated between a lower collar 122, having male threads, and a female collar 114, having female threads. The lower collar 122 is fitted with a Luer lock that allows; it to be readily secured to the syringe 112 and the upper collar 114 is fitted with a needle 102.

In preferred embodiments, the lipid solution is extruded through a filter and the lipid solution is heat sterilized prior to shaking. Once gas-filled liposomes are formed, they may be filtered for sizing as described above. These steps prior to the formation of gas-filled liposomes provide the advantages, for example, of reducing the amount of unhydrated lipid and thus providing a significantly higher yield of gas-filled liposomes, as well as and providing sterile gas-filled liposomes ready for administration to a patient. For example, a mixing vessel such as a vial or syringe may be filled with a filtered lipid suspension, and the solution may then be sterilized within the mixing vessel, for example, by autoclaving. Gas may be instilled into the lipid suspension to form gas-filled liposomes by shaking the sterile vessel. Preferably, the sterile vessel is equipped with a filter positioned such that the gas-filled liposomes pass through the filter before contacting a patient.

Figure 7A:
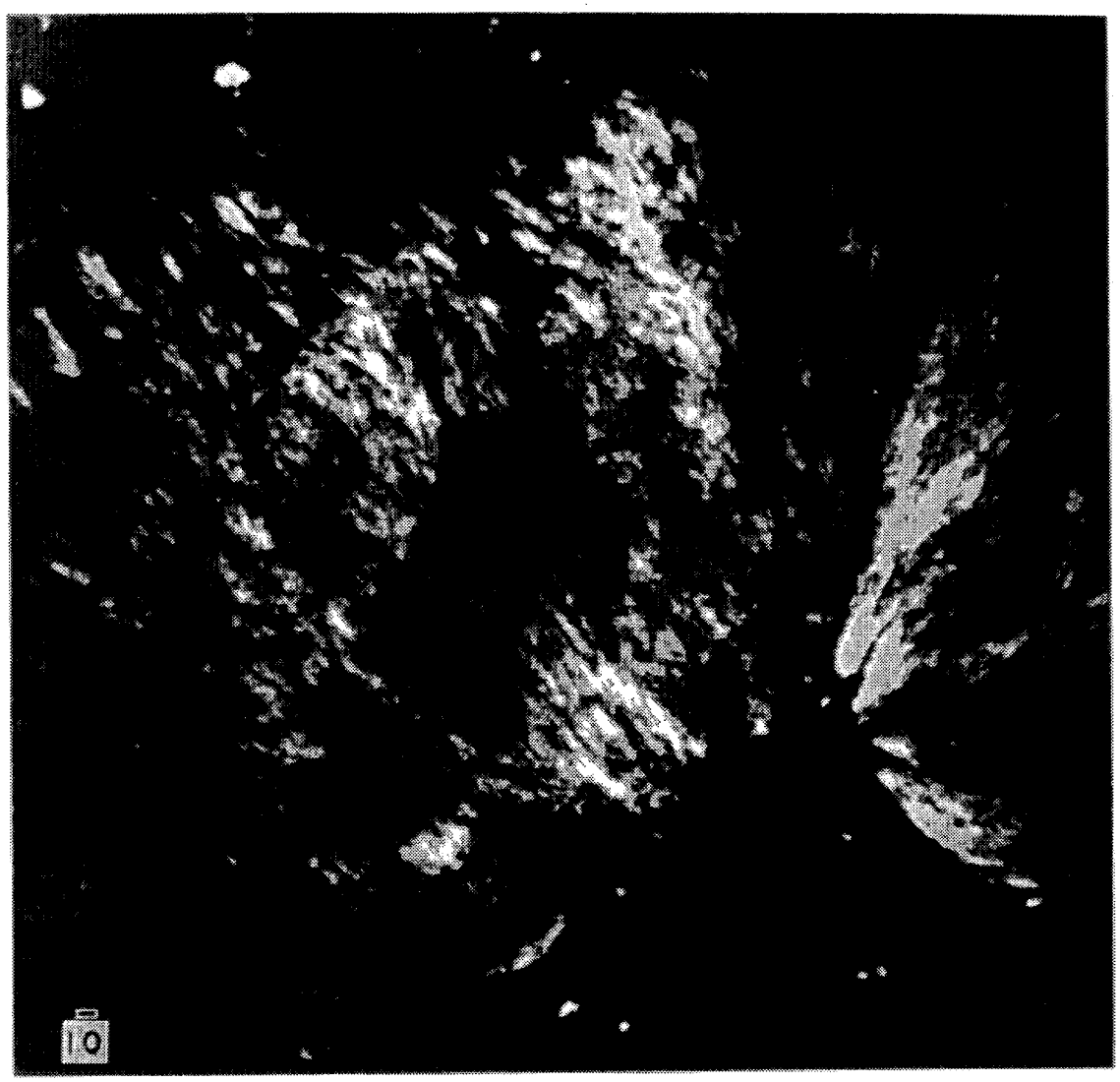
FIG. 7 is a micrograph of a lipid suspension before (A) and after (B) extrusion through a filter.
Figure 7B:
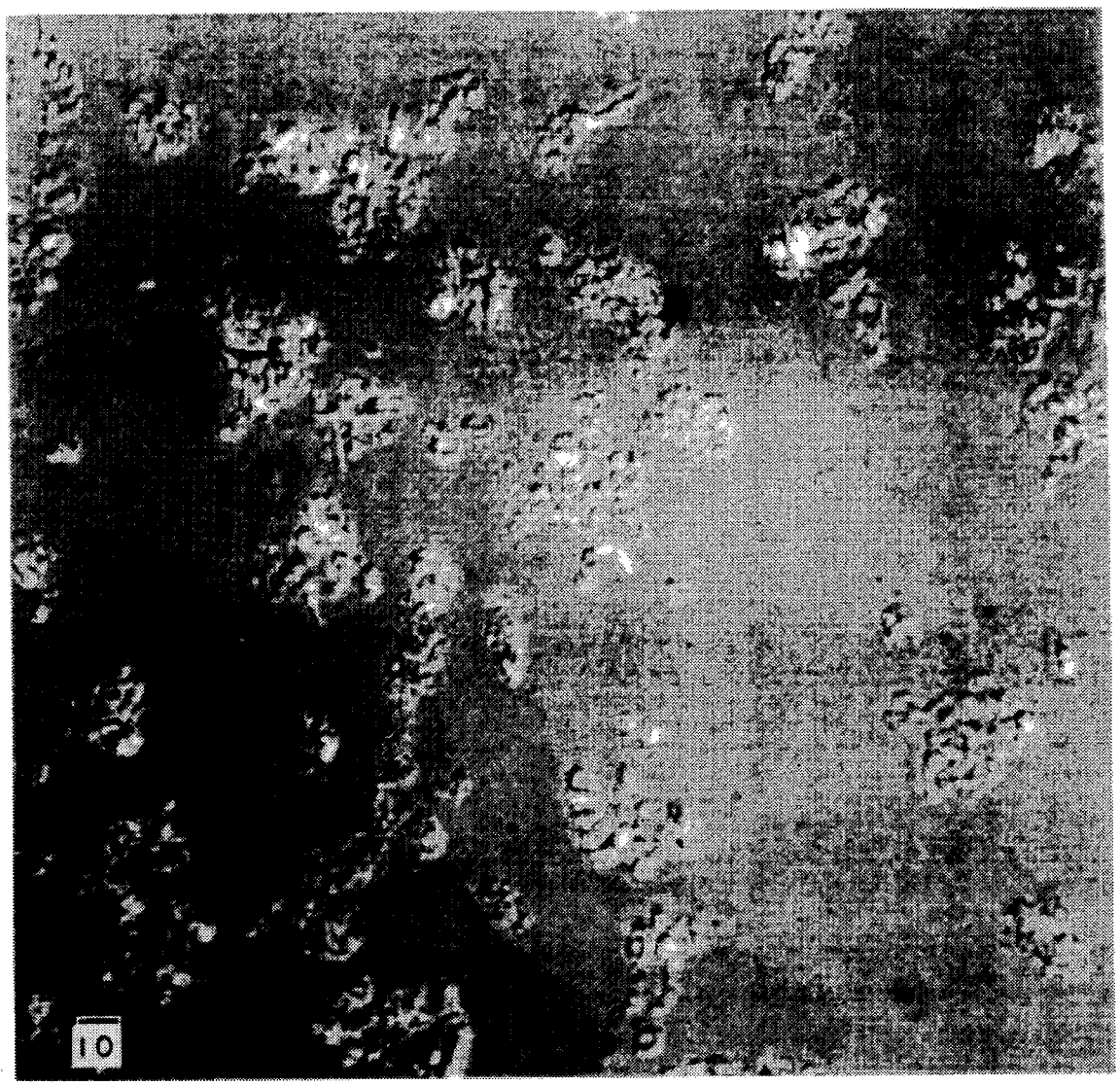

The first step of this preferred method, extruding the lipid solution through a filter, decreases the amount of unhydrated lipid by breaking up the dried lipid and exposing a greater surface area for hydration. Preferably, the filter has a pore size of about 0.1 to about 5 μm, more preferably, about 0.1 to about 4 μm, even more preferably, about 0.1 to about 2 μm, and most preferably, about 1 μm. As shown in FIG. 7, when a lipid suspension is filtered (FIG. 7B), the amount of unhydrated lipid is reduced when compared to a lipid suspension that was not pre-filtered (FIG. 7A). Unhydrated lipid appears as amorphous clumps of non-uniform size and is undesirable.

The second step, sterilization, provides a composition that may be readily administered to a patient. Preferably, sterilization is accomplished by heat sterilization, preferably, by autoclaving the solution at a temperature of at least about 100° C., and more preferably, by autoclaving at about 100° C. to about 130° C., even more preferably, about 110° C. to about 130° C., even more preferably, about 120° C. to about 130° C., and most preferably, about 130° C. Preferably, heating occurs for at least about 1 minute, more preferably, about 1 to about 30 minutes, even more preferably, about 10 to about 20 minutes, and most preferably, about 15 minutes.

Where sterilization occurs by a process other than heat sterilization at a temperature which would cause rupture of the gas-filled liposomes, sterilization may occur subsequent to the formation of the gas-filled liposomes, and is preferred. For example, gamma radiation may be used before and/or after gas-filled liposomes are formed.

Figure 8A:
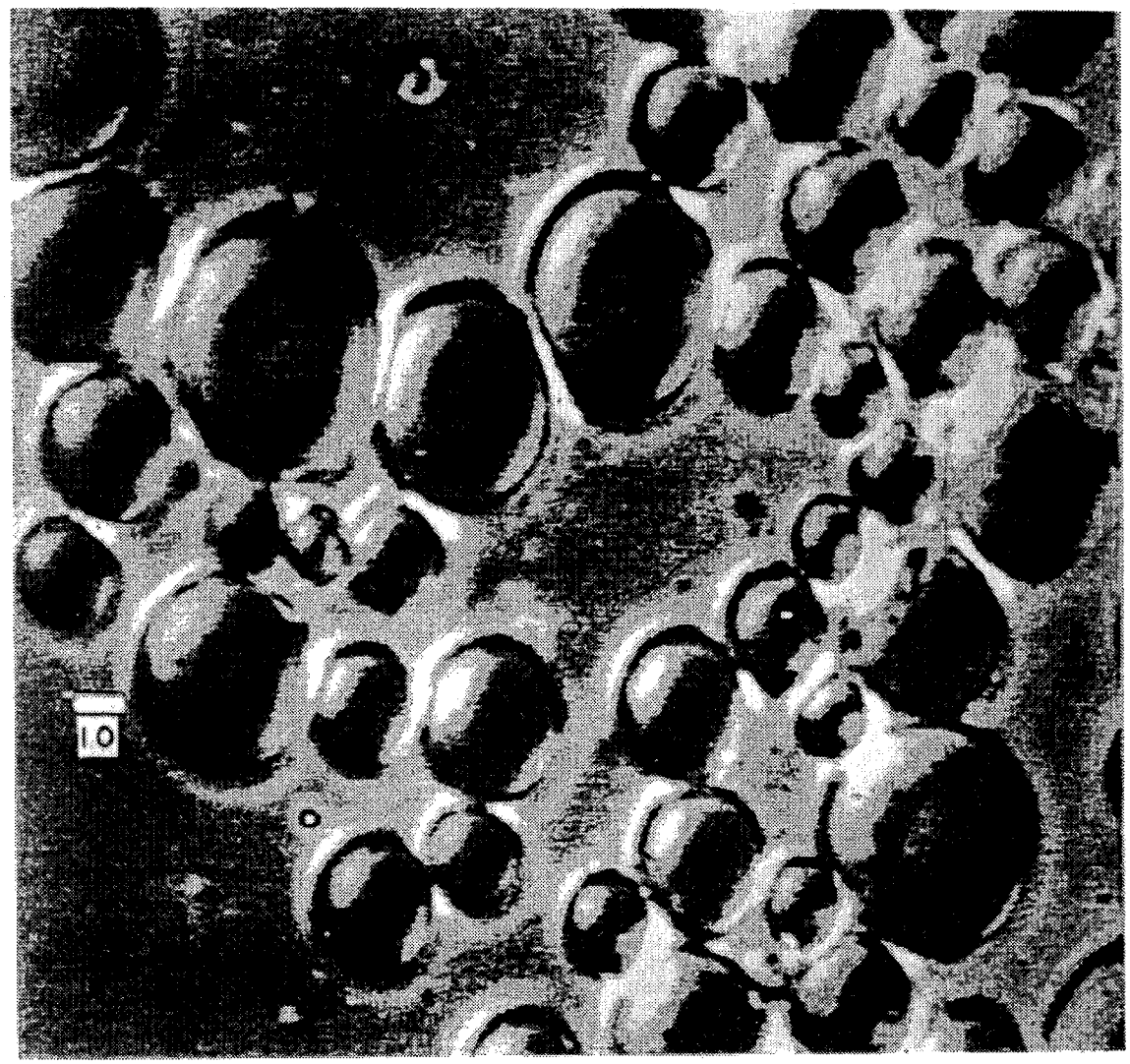
FIG. 8 is a micrograph of gas-filled liposomes formed subsequent to filtering and autoclaving a lipid suspension, the micrographs having been taken before (A) and after (B) sizing by filtration of the gas-filled liposomes.
Figure 8B:
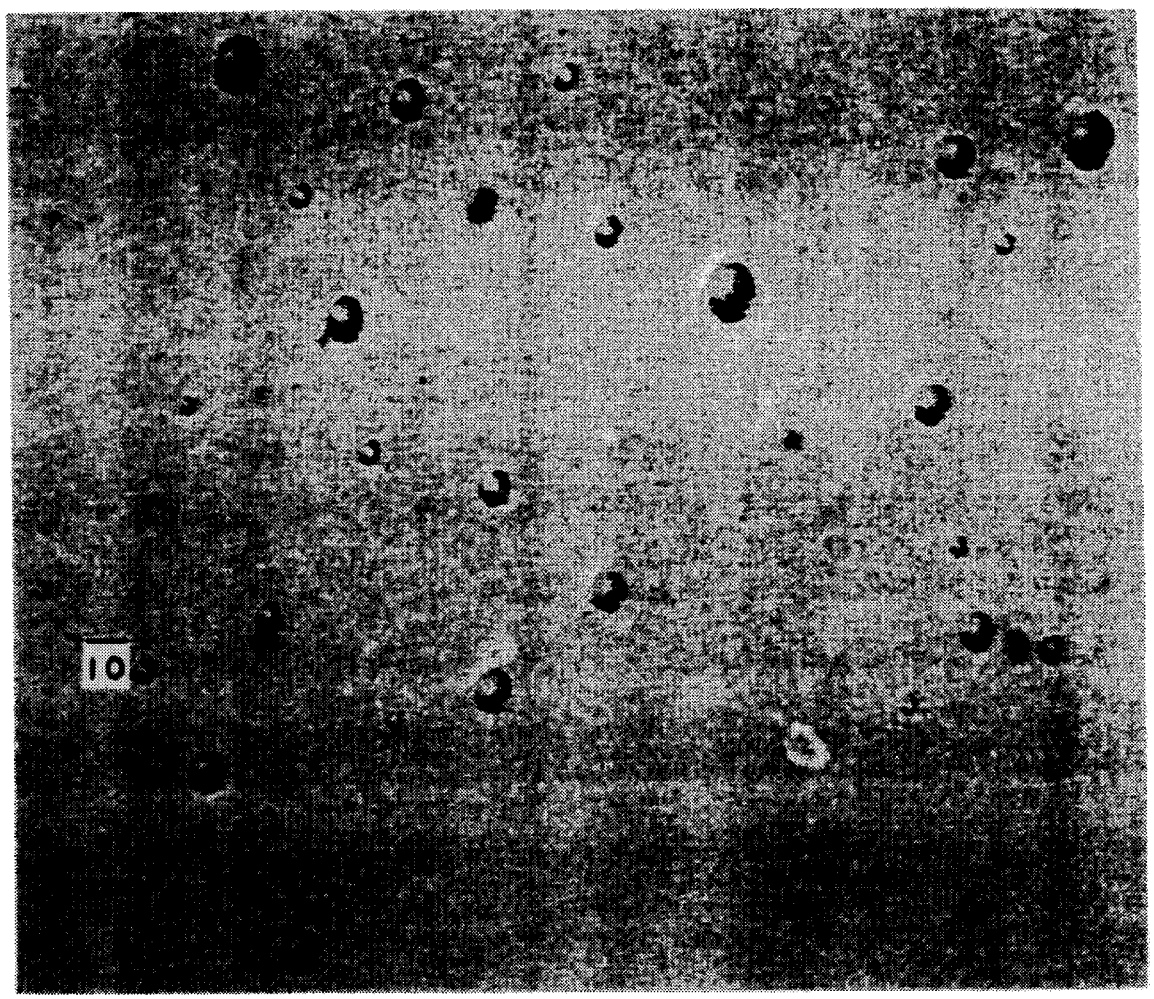

FIG. 8 illustrates the ability of gas-filled liposomes to successfully form after autoclaving, which was carried out at 130° C. for 15 minutes, followed by vortexing for 10 minutes. Further, after the extrusion and sterilization procedure, the shaking step yields gas-filled liposomes with little to no residual anhydrous lipid phase. FIG. 8A shows gas-filled liposomes generated after autoclaving but prior to filtration, thus resulting in a number of gas-filled liposomes having a size greater than 10 μm. FIG. 8B shows gas-filled liposomes after a filtration through a 10 μm "NUCLEPORE" filter, resulting in a uniform size around 10 μm.

The materials which may be utilized in preparing the gas-filled lipid microspheres include any of the materials or combinations thereof known to those skilled in the art as suitable for liposome preparation. The lipids used may be of either natural or synthetic origin. The particular lipids are chosen to optimize the desired properties, e.g., short plasma half-life versus long plasma half-life for maximal serum stability. It will also be understood that certain lipids may be more efficacious for particular applications, such as the containment of a therapeutic compound to be released upon rupture of the gas-filled lipid microsphere.

The lipid in the gas-filled liposomes may be in the form of a single bilayer or a multilamellar bilayer, and are preferably multilamellar.

Lipids which may be used to create lipid microspheres include but are not limited to: lipids such as fatty acids, lysolipids, phosphatidylcholine with both saturated and unsaturated lipids including dioleoylphosphatidylcholine; dimyristoylphosphatidylcholine; dipentadecanoylphosphatidylcholine, dilauroylphosphatidylcholine, dipalmitoylphosphatidylcholine; distearoylphosphatidylcholine; phosphatidylethanolamines such as dioleoylphosphatidylethanolamine; phosphatidylserine; phosphatidylglycerol; phosphatidylinositol, sphingolipids such as sphingomyelin; glycolipids such as ganglioside GM1 and GM2; glucolipids; sulfatides; glycosphingolipids; phosphatidic acid; palmitic acid; stearic acid; arachidonic acid; oleic acid; lipids bearing polymers such as polyethyleneglycol, chitin, hyaluronic acid or polyvinylpyrrolidone; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids, polymerized lipids, diacetyl phosphate, stearylamine, cardiolipin, phospholipids with short chain fatty acids of 6–8 carbons in length, synthetic phospholipids with asymmetric acyl chains (e.g., with one acyl chain of 6 carbons and another acyl chain of 12 carbons), 6-(5-cholesten-3β-yloxy)-1-thio-β-D-galactopyranoside, digalactosyldiglyceride, 6-(5-cholesten-3β-yloxy)hexyl-6-amino-6-deoxy-1-thio-β-D-galactopyranoside, 6-(5-cholesten-3β-yloxy)hexyl-6-amino-6-deoxy-1-thio-β-D-mannopyranoside, 12-(((7'-diethylaminocoumarin-3-yl)carbonyl)methylamino)-octadecanoic acid; N-[12-(((7'-diethylaminocoumarin-3-yl)carbonyl)methyl-amino)octadecanoyl]-2-aminopalmitic acid; cholesteryl)4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol;1-hexadecyl-2-palmitoylglycerophosphoethanolamine; and palmitoylhomocysteine; and/or combinations thereof.

If desired, a variety of cationic lipids such as DOTMA, N-[1-(2,3-dioleoyloxy)propyl]-N,N,N-trimethylammonium chloride; DOTAP, 1,2-dioleoyloxy-3-(trimethylammonio)propane; and DOTB, 1,2-dioleoyl-3-(4"-trimethyl-ammonio)butanoyl-sn-glycerol may be used. In general the molar ratio of cationic lipid to non-cationic lipid in the liposome may be, for example, 1:1000, 1:100, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid when cationic lipid is used to construct the microsphere. Preferably, this non-cationic lipid is dipalmitoylphosphatidylcholine, dipalmitoylphosphatidylethanolamine or dioleoylphosphatidylethanolamine. In lieu of cationic lipids as described above, lipids bearing cationic polymers such as polylysine or polyarginine may also be used to construct the microspheres and afford binding of a negatively charged therapeutic, such as genetic material, to the outside of the microspheres. Additionally, negatively charged lipids may be used, for example, to bind positively charged therapeutic compounds.

Other useful lipids or combinations thereof apparent to those skilled in the art which are in keeping with the spirit of the present invention are also encompassed by the present invention. For example, carbohydrate-bearing lipids may be employed for in vivo targeting, as described in U.S. Pat. No. 4,310,505, the disclosures of which are hereby incorporated herein by reference in their entirety.

The most preferred lipids are phospholipids, preferably DPPC and DSPC, and most preferably DPPC.

Saturated and unsaturated fatty acids that may be used to generate gas-filled microspheres preferably include, but are not limited to molecules that have between 12 carbon atoms and 22 carbon atoms in either linear or branched form. Examples of saturated fatty acids that may be used include, but are not limited to, lauric, myristic, palmitic, and stearic acids. Examples of unsaturated fatty acids that may be used include, but are not limited to, lauroleic, physeteric, myristoleic, palmitoleic, petroselinic, and oleic acids. Examples of branched fatty acids that may be used include, but are not limited to, isolauric, isomyristic, isopalmitic, and isostearic acids and isoprenoids.

Cationic polymers may be bound to the lipid layer through one or more alkyl groups or sterol groups which serve to anchor the cationic polymer into the lipid layer surrounding the gas. Cationic polymers that may be used in this manner include, but are not limited to, polylysine and polyarginine, and their analogs such as polyhomoarginine or polyhomolysine. The positively charged groups of cationic lipids and cationic polymers, or perfluoroalkylated groups bearing cationic groups, for example, may be used to complex negatively charged molecules such as sugar phosphates on genetic material, thus binding the material to the surface of the gas-filled lipid sphere. For example, cationic analogs of amphiphilic perfluoroalk]{lated bipyridines, as described in Garelli and Vierling, *Biochim. Biophys Acta,* 1992 1127, 41–48, the disclosures of which are hereby incorporated herein by reference in their entirety, may be used. Alternatively, for example, negatively charged molecules may be bound directly to the head groups of the lipids via ester, amide, ether, disulfide or thioester linkages.

Bioactive materials, such as peptides or proteins, may be incorporated into the lipid layer provided the peptides have sufficient lipophilicity or may be derivatized with alkyl or sterol groups for attachment to the lipid layer. Negatively charged peptides may be attached, for example, using cationic lipids or polymers as described above.

Solutions of lipids or gas-filled liposomes may be stabilized, for example, by the addition of a wide variety of viscosity modifiers, including, but not limited to carbohydrates and their phosphorylated and sulfonated derivatives; polyethers, preferably with molecular weight ranges between 400 and 8000; di- and trihydroxy alkanes and their polymers, preferably with molecular weight ranges between 800 and 8000. Emulsifying and/or solubilizing agents may also be used in conjunction with lipids or liposomes. Such agents include, but area not limited to, acacia, cholesterol, diethanolamine,, glyceryl monostearate, lanolin alcohols, lecithin, mono- and di-glycerides, mono-ethanolamine, oleic acid, oleyl alcohol, poloxamer, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax. Suspending and/or viscosity-increasing agents that may be used with lipid or liposome solutions include but are not limited to, acacia, agar, alginic acid, aluminum monostearate, bentonite, magma, carbomer 934P, carboxymethylcellulose, calcium and sodium and sodium 12, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol alginate, silicon dioxide, sodium alginate, tragacanth, and xanthum gum.

The gas-filled liposomes of the present invention are preferably comprised of an impermeable material. Impermeable material is defined a material that does not permit the passage of a substantial amount of the contents of the liposome in typical storage conditions. Substantial is defined as greater than about 50% of the contents, the contents being both the gas as well as any other component encapsulated within the interior of the liposome, such as a therapeutic. Preferably, no more than about 25% of the gas is released, more preferably, no more than about 10% of the gas is released, and most preferably, no more than about 1% of the gas is released during storage and prior to administration to a patient.

At least in part, the gas impermeability of gas-filled liposomes has been found to be related to the gel state to liquid crystalline state phase transition temperature. It is believed that, generally, the higher gel state to liquid crystalline state phase transition temperature, the more gas impermeable the liposomes are at a given temperature. See Table I above and Derek Marsh, *CRC Handbook of Lipid Bilayers* (CRC Press, Boca Raton, Fla. 1990), at p. 139 for main chain melting transitions of saturated diacyl-sn-glycero-3-phosphocholines. However, it should be noted that a lesser degree of energy can generally be used to release a therapeutic compound from gas-filled liposomes composed of lipids with a lower gel state to liquid crystalline state phase transition temperature.

In certain preferred embodiments, the phase transition temperature of the lipid is greater than the internal body temperature of the patient to which they are administered. For example, lipids having a phase transition temperature greater than about 37° C. are preferred for administration to humans. In general, microspheres having a phase transition temperature greater than about 20° C. are preferred.

In preferred embodiments, the liposomes made by the methods of the present invention are stable, stability being defined as resistance to rupture from the time of formation until the application of ultrasound. The lipids used to construct the microspheres may be chosen for stability. For example, gas-filled liposomes composed of DSPC (distearoylphosphatidylcholine) are more stable than gas-filled liposomes composed of DPPC (dipalmitoylphosphatidylcholine) and that these in turn are more stable than gas-filled liposomes composed of egg phosphatidylcholine (EPC). Preferably, no more than about 50% of the liposomes rupture from the time of formation until the application of ultrasound, more preferably., no more than about 25% of the liposomes rupture, even more preferably, no more than about 10% of the liposomes, and most preferably, no more than about 1% of the liposomes.

The subject liposomes tend to have greater gas impermeability and stability during storage than other gas-filled liposomes produced via known procedures such as pressurization or other techniques. At 72 hours after formation, for example, conventionally prepared liposomes often are essentially devoid of gas, the gas having diffused out of the liposomes and/or the liposomes having ruptured and/or fused, resulting in a concomitant loss in reflectivity. In comparison, gas-filled liposomes of the present invention maintained in aqueous solution generally have a shelf life stability of greater than about three weeks, preferably a shelf life stability of greater than about four weeks, more preferably a shelf life stability of greater than about five weeks, even more preferably a shelf life stability of greater than about three months, and often a shelf life stability that is even much longer, such as over six months, twelve months, or even two years.

In addition, it has been found that the incorporation of at least a small amount of negatively charged lipid into any liposome membrane, although not required, is beneficial to providing liposomes that do not have a propensity to rupture by aggregation. By at least a small amount, it is meant about 1 mole percent of the total lipid. Suitable negatively charged lipids will be readily apparent to those skilled in the art, and include, for example, phosphatidylserine and fatty acids. Most preferred for ability to rupture on application of resonant frequency ultrasound, echogenicity and stability are liposomes prepared from dipalmitoylphosphatidylcholine.

Further, the liposomes of the invention are preferably sufficiently stable in the vasculature such that they withstand recirculation. The gas-filled liposomes may be coated such that uptake by the reticuloendothelial system is minimized. Useful coatings include, for example, gangliosides, glucuronide, galacturonate, guluronate, polyethyleneglycol, polypropylene glycol, polyvinylpyrrolidone, polyvinylalcohol, dextran, starch, phosphorylated and sulfonated mono, di, tri, oligo and polysaccharides and albumin. The liposomes may also be coated for purposes such as evading recognition by the immune system.

The lipid used is also preferably flexible. Flexibility, as defined in the context of gas-filled liposomes, is the ability of a structure to alter its shape, for example, in order to pass through an opening having a size smaller than the liposome.

Provided that the circulation half-life of the liposomes is sufficiently long, the liposomes will generally pass through the target tissue while passing through the body. Thus, by focusing the sound waves on the selected tissue to be treated, the therapeutic will be released locally in the target tissue. As a further aid to targeting, antibodies, carbohydrates, peptides, glycopeptides, glycolipids and lectins may also be incorporated into the surface of the liposomes. Other aids for targeting include polymers such as polyethyleneglycol, polyvinylpyrrolidone, and polyvinylalcohol, which may be incorporated onto the surface via alkylation, acylation, sterol groups or derivatized head groups of phospholipids such as dioleoylphosphatidylethanolamine. Peptides, antibodies, lectins, glycopeptides, oligonucleotides, and glycoconjugates may also be incorporated onto the surfaces of the gas-filled lipid spheres.

In certain preferred embodiments, as an aid to the gas installation process as well as to maintain the stability of the gas-filled liposomes, for example, emulsifiers may be added to the lipid. Examples of emulsifiers include, but are not limited to, glycerol, cetyl alcohol, sorbitol, polyvinyl alcohol, polypropylene glycol, propylene glycol, ethyl alcohol, sodium lauryl sulfate, Laureth 23, polysorbates (all units), all saturated and unsaturated fatty acids, and triethanolamine.

For storage prior to use, the liposomes of the present invention may be suspended in an aqueous solution, such as a saline solution (for example, a phosphate buffered saline solution), or simply water, and stored preferably at a temperature of between about 2° C. and about 10° C., preferably at about 4° C. Preferably, the water is sterile.

Typical storage conditions are, for example, a non-degassed aqueous solution of 0.9% NaCl maintained at 4° C. for 48 hours. The temperature of storage is preferably below the gel state to liquid crystalline state phase transition temperature of the material forming the liposomes.

Most preferably, the liposomes are stored in an isotonic saline solution, although, if desired, the saline solution may be hypotonic (e.g., about 0.3 to about 0.5% NaCl). The solution also may be buffered, if desired, to provide a pH range of about pH 5 to about pH 7.4. Suitable buffers include, but are not limited to, acetate, citrate, phosphate and bicarbonate.

Bacteriostatic agents may also be included with the liposomes to prevent bacterial degradation on storage. Suitable bacteriostatic agents include but are not limited to benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate., sodium benzoate and sorbic acid.

By "gas-filled" as used herein, it is meant liposomes having an interior volume that is at least about 10% gas, preferably at least about 25% gas, more preferably at least about 50% gas, even more preferably at least about 75% gas, and most preferably at least about 90% gas. It will be understood by one skilled in the art, once armed with the present disclosure, that a gaseous precursor may also be used, followed by activation to form a gas.

Various biocompatible gases may be employed in the gas-filled liposomes of the present invention. Such gases include air, nitrogen, carbon dioxide, oxygen, argon, fluorine, xenon, neon, helium, or any and all combinations thereof. Other suitable gases will be apparent to those skilled in the art once armed with the present disclosure.

The size of the liposomes of the present invention will depend upon the intended use. With the smaller liposomes, resonant frequency ultrasound will generally be higher than for the larger liposomes. Sizing also serves to modulate resultant liposomal biodistribution and clearance. In addition to filtration, the size of the liposomes can be adjusted, if desired, by procedures known to one skilled in the art, such as extrusion, sonication, homogenization, the use of a laminar stream of a core of liquid introduced into an immiscible sheath of liquid. See, for example, U.S. Pat. No. 4,728,578; U.K. Patent Application GB 2193095 A; U.S. Pat. No. 4,728,575; U.S. Pat. No. 4,737,323; International Application PCT/US85/01161; Mayer et al., *Biochimica et Biophysica Acta* 1986, 858, 161–168; Hope et al., *Biochimica et Biophysica Acta* 1985, 812, 55–65; U.S. Pat. No. 4,533,254; Mayhew et al., *Methods in Enzymology* 1987, 149, 64–77; Mayhew et al., *Biochimica et Biophysica Acta* 1984, 755, 169–74; Cheng et al, *Investigative Radiology* 1987, 22, 47–55; PCT/US89/05040; U.S. Pat. No. 4,162,282; U.S. Pat. No. 4,310,505; U.S. Pat. No. 4,921,706; and *Liposomes Technology*, Gregoriadis, G., ed., Vol. I, pp. 29–37, 51–67 and 79–108 (CRC Press Inc, Boca Raton, Fla., 1984). The disclosures of each of the foregoing patents, publications and patent applications are incorporated by reference herein, in their entirety. Extrusion under pressure through pores of defined size is a preferred method of adjusting the size of the liposomes.

Since liposome size influences biodistribution, different size liposomes may be selected for various purposes. For example, for intravascular application, the preferred size range is a mean outside diameter between about 30 nanometers and about 10 microns, with the preferable mean outside diameter being about 5 microns.

More specifically, for intravascular application, the size of the liposomes is preferably about 10 µm or less in mean outside diameter, and preferably less than about 7 µm, and more preferably less than about 5 µm in mean outside diameter. Preferably, the liposomes are no smaller than about 30 nanometers in mean outside diameter.

To provide therapeutic delivery to organs such as the liver and to allow differentiation of tumor from normal tissue, smaller liposomes, between about 30 nanometers and about 100 nanometers in mean outside diameter, are preferred.

For embolization of a tissue such as the kidney or the lung, the liposomes are preferably less than about 200 microns in mean outside diameter.

For intranasal, intrarectal or topical administration, the microspheres are preferably less than about 100 microns in mean outside diameter.

Large liposomes, e.g., between 1 and 10 microns in size, will generally be confined to the intravascular space until they are cleared by phagocytic elements lining the vessels, such as the macrophages and Kuppfer cells lining capillary sinusoids. For passage to the cells beyond the sinusoids, smaller liposomes, for example, less than about a micron in mean outside diameter, e.g., less than about 300 nanometers in size, may be utilized.

The route of administration of the liposomes will vary depending on the intended use. As one skilled in the art would recognize, administration of therapeutic delivery systems of the present invention may be carried out in various fashions, such as intravascularly, intralymphatically, parenterally, subcutaneously, intramuscularly, intranasally, intrarectally, intraperitoneally, interstitially, into the airways via nebulizer, hyperbarically, orally, topically, or intratumorly, using a variety of dosage forms. One preferred route of administration is intravascularly. For intravascular use, the therapeutic delivery system is generally injected intravenously, but may be injected intraarterially as well. The liposomes of the invention may also be injected interstitially or into any body cavity.

The delivery of therapeutics from the liposomes of the present invention using ultrasound is best accomplished for tissues which have a good acoustic window for the transmission of ultrasonic energy. This is the case for most tissues in the body such as muscle, the heart, the liver and most other vital structures. In the brain, in order to direct the ultrasonic energy past the skull a surgical window may be necessary.

Additionally, the invention is especially useful in delivering therapeutics to a patient's lungs. Gas-filled liposomes of the present invention are lighter than, for example, conventional liquid-filled liposomes which generally deposit in the central proximal airway rather than reaching the periphery of the lungs. It is therefore believed that the gas-filled liposomes of the present invention may improve delivery of a therapeutic compound to the periphery of the lungs, including the terminal airways and the alveoli. For application to the lungs, the gas-filled liposomes may be applied through nebulization, for example.

In applications such as the targeting of the lungs, which are lined with lipids, the therapeutic may be released upon aggregation of the gas-filled liposome with the lipids lining the targeted tissue. Additionally, the gas-filled liposomes may burst after administration without the use of ultrasound. Thus, ultrasound need not be applied to release the drug in the above type of administration.

Further, the gas-filled liposomes of the invention are especially useful for therapeutics that may be degraded in aqueous media or upon exposure to oxygen and/or atmospheric air. For example, the liposomes may be filled with an inert gas such as nitrogen or argon, for use with labile therapeutic compounds. Additionally, the gas-filled liposomes may be filled with an inert gas and used to encapsulate a labile therapeutic for use in a region of a patient that would normally cause the therapeutic to be exposed to atmospheric air, such as cutaneous and ophthalmic applications.

The gas-filled liposomes are also especially useful for transcutaneous delivery, such as a patch delivery system. The use of rupturing ultrasound may increase transdermal delivery of therapeutic compounds. Further, a mechanism may be used to monitor and modulate drug delivery. For example, diagnostic ultrasound may be used to visually monitor the bursting of the gas-filled liposomes and modulate drug delivery and/or a hydrophone may be used to detect the sound of the bursting of the gas-filled liposomes and modulate drug delivery.

In preferred embodiments, the liposomes are administered individually, rather than embedded in a matrix, for example.

For in vitro use, such as cell culture applications, the gas-filled liposomes may be added to the cells in cultures and then incubated. Subsequently sonic energy can be applied to the culture media containing the cells and liposomes.

Generally, the therapeutic delivery systems of the invention are administered in the form of an aqueous suspension such as in water or a saline solution (e.g., phosphate buffered saline). Preferably, the water is sterile. Also, preferably the saline solution is an isotonic saline solution, although, if desired, the saline solution may be hypotonic (e.g., about 0.3 to about 0.5% NaCl). The solution may also be buffered, if desired, to provide a pH range of about. pH 5 to about pH 7.4. In addition, dextrose may be preferably included in the media. Further solutions that may be used for administration of gas-filled liposomes include, but are not limited to almond oil, corn oil, cottonseed oil, ethyl oleate, isopropyl myristate, isopropyl palmitate, mineral oil, myristyl alcohol, octyldodecanol, olive oil, peanut oil, persic oil, sesame oil, soybean oil, and squalene.

The useful dosage of gas-filled microspheres to be administered and the mode of administration will vary depending upon the age, weight, and mammal to be treated, and the particular application (therapeutic/diagnostic) intended. Typically, dosage is initiated at lower levels and increased until the desired therapeutic effect is achieved.

For use in ultrasonic imaging, preferably, the liposomes of the invention possess a reflectivity of greater than 2 dB, more preferably between about 4 dB and about 20 dB. Within these ranges, the highest reflectivity for the liposomes of the invention :is exhibited by the larger liposomes, by higher concentrations of liposomes, and/or when higher ultrasound frequencies are employed.

For therapeutic drug delivery, the rupturing of the therapeutic containing liposomes of the invention is surprisingly easily carried out by applying ultrasound of a certain frequency to the region of the patient where therapy is desired, after the liposomes have been administered to or have otherwise reached that region. Specifically, it has been unexpectedly found that when ultrasound is applied at a frequency corresponding to the peak resonant frequency of the therapeutic containing gas-filled liposomes, the liposomes will rupture and release their contents.

The peak resonant frequency can be determined either in vivo or in vitro, but preferably in vivo, by exposing the liposomes to ultrasound, receiving the reflected resonant frequency signals and analyzing the spectrum of signals received to determine the peak, using conventional means. The peak, as so determined, corresponds to the peak resonant frequency (or second harmonic, as it is sometimes termed).

Preferably, the liposomes of the invention have a peak resonant frequency of between about 0.5 mHz and about 10 mHz. Of course, the peak resonant frequency of the gas-filled liposomes of the invention will vary depending on the outside diameter and, to some extent, the elasticity or flexibility of the liposomes, with the larger and more elastic or flexible liposomes having a lower resonant frequency than the smaller and less elastic or flexible liposomes.

The therapeutic-containing gas-filled liposomes will also rupture when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and therapeutic release is improved, appreciable tissue heating does not generally occur (frequently no increase in temperature above about 2° C.), and less overall energy is required. Thus, application of ultrasound at the peak resonant frequency, while not required, is most preferred.

For diagnostic or therapeutic ultrasound, any of the various types of diagnostic ultrasound imaging devices may be employed in the practice of the invention, the particular type or model of the device not being critical to the method of the invention. Also suitable are devices designed for administering ultrasonic hyperthermia, such devices being described in U.S. Pat. Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, and then intensity, time, and/or resonant frequency increased until the liposome is visualized on ultrasound (for diagnostic ultrasound applications) or ruptures (for therapeutic ultrasound applications).

Although application of the various principles will be readily apparent to one skilled in the art, once armed with the present disclosure, by way of general guidance, for gas-filled liposomes of about 1.5 to about 10 microns in mean outside diameter, the resonant frequency will generally be in the range of about 1 to about 10 megahertz. By adjusting the focal zone to the center of the target tissue (e.g., the tumor) the gas-filled liposomes can be visualized under real time ultrasound as they accumulate within the target tissue. Using the 7.5 megahertz curved array transducer as an example, adjusting the power delivered to the transducer to maximum and adjusting the focal zone within the target tissue, the spatial peak temporal average (SPTA) power will then be a maximum of approximately 5.31 mW/cm$^2$ in water. This power will cause some release of therapeutic from the gas-filled liposomes, but much greater release can be accomplished by using higher power.

By switching the transducer to the doppler mode, higher power outputs are available, up to 2.5 watts per cm$^2$ from the same transducer. With the machine operating in doppler mode, the power can be delivered to a selected focal zone within the target tissue and the gas-filled liposomes can be made to release their therapeutics. Selecting the transducer to match the resonant frequency of the gas-filled liposomes will make this process of therapeutic release even more efficient.

For larger diameter gas-filled liposomes, e.g., greater than 3 microns in mean outside diameter, a lower frequency transducer may be more effective in accomplishing therapeutic release. For example, a lower frequency transducer of 3.5 megahertz (20 mm curved array model) may be selected to correspond to the resonant frequency of the gas-filled liposomes. Using this transducer, 101.6 milliwatts per cm$^2$ may be delivered to the focal spot, and switching to doppler mode will increase the power output (SPTA) to 1.02 watts per cm$^2$.

To use the phenomenon of cavitation to release and/or activate the drugs/prodrugs within the gas-filled liposomes, lower frequency energies may be used, as cavitation occurs more effectively at lower frequencies. Using a 0.757 megahertz transducer driven with higher voltages (as high as 300 volts) cavitation of solutions of gas-filled liposomes will occur at thresholds of about 5.2 atmospheres.

Table II shows the ranges of energies transmitted to tissues from diagnostic ultrasound on commonly used instruments such as the Piconics Inc. (Tyngsboro, Mass.) Portascan general purpose scanner with receiver pulser 1966 Model 661; the Picker (Clewsland, Ohio) Echoview 8L Scanner including 80C System or the Medisonics (Mountain View, Calif.) Model D-9 Versatone Bidirectional Doppler. In general, these ranges of energies employed in pulse repetition are useful for diagnosis and monitoring:the gas-filled liposomes but are insufficient to rupture the gas-filled liposomes of the present invention.

TABLE II

Power and Intensities Produced by Diagnostic Equipment*

| Pulse repetition rate (Hz) | Total ultrasonic power output P (mW) | Average Intensity at transducer face $I_{TD}$ (W/m$^2$) |
|---|---|---|
| 520 | 4.2 | 32 |
| 676 | 9.4 | 71 |
| 806 | 6.8 | 24 |
| 1000 | 14.4 | 51 |
| 1538 | 2.4 | 8.5 |

*Values obtained from Carson et al., Ultrasound in Med. & Biol. 1978 3, 341–350, the disclosures of which are hereby incorporated herein by reference in their entirety.

Higher energy ultrasound such as commonly employed in therapeutic ultrasound equipment is preferred for activation of the therapeutic containing gas-filled liposomes. In general, therapeutic ultrasound machines employ as much as 50% to 100% duty cycles dependent upon the area of tissue to be heated by ultrasound. Areas with larger amounts of muscle mass (i.e., backs, thighs) and highly vascularized tissues such as heart may require the larger duty cycle, e.g., 100%.

In diagnostic ultrasound, one or several pulses of sound are used and the machine pauses between pulses to receive the reflected sonic signals. The limited number of pulses used in diagnostic ultrasound limits the effective energy which is delivered to the tissue which is being imaged.

In therapeutic ultrasound, continuous wave ultrasound is used to deliver higher energy levels. In using the liposomes of the present invention, the sound energy may be pulsed, but continuous wave ultrasound is preferred. If pulsing is employed, the sound will preferably be pulsed in echo train lengths of at least about 8 and preferably at least about 20 pulses at a time.

Either fixed frequency or modulated frequency ultrasound may be used. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Focused, frequency modulated, high energy ultrasound may increase the rate of local gaseous expansion within the liposomes and rupturing to provide local delivery of therapeutics.

The frequency of the sound used may vary from about 0.025 to about 100 megahertz. Frequency ranges between about 0.75 and about 3 megahertz are preferred and frequencies between about 1 and about 2 megahertz are most preferred. Commonly used therapeutic frequencies of about 0.75 to about 1.5 megahertz may be used. Commonly used diagnostic frequencies of about 3 to about 7.5 megahertz may also be used. For very small liposomes, e.g., below 0.5 micron in mean outside diameter, higher frequencies of sound may be preferred as these smaller liposomes will absorb sonic energy more effectively at higher frequencies of sound. When very high frequencies are used, e.g., over 10 megahertz, the sonic energy will generally have limited depth penetration into fluids and tissues. External application may be preferred for the skin and other superficial tissues, but for deep structures, the application of sonic energy via interstitial probes or intravascular ultrasound catheters may be preferred.

Where the gas-filled liposomes are used for drug delivery, the therapeutic drug compound to be delivered may be embedded within the wall of the liposome, encapsulated in the liposome and/or attached to the liposome, as desired. The phrase "attached to" or variations thereof, as used herein in connection with the location of the therapeutic compound, means that the therapeutic compound is linked in some manner to the inside and/or the outside wall of the microsphere, such as through a covalent or ionic bond or other means of chemical or electrochemical linkage or interaction. The phrase "encapsulated in variations thereof" as used in connection with the location of the therapeutic compound denotes that the therapeutic compound is located in the internal microsphere void. The phrase "embedded within" or variations thereof as used in connection with the location of the therapeutic compound, signifies the positioning of the therapeutic compound within the microsphere wall. The phrase "comprising a therapeutic" denotes all of the varying types of therapeutic positioning in connection with the microsphere. Thus, the therapeutic can be positioned variably, such as, for example, entrapped within the internal void of the gas-filled microsphere, situated between the gas and the internal wall of the gas-filled microsphere, incorporated onto the external surface of the gas-filled microsphere and/or enmeshed within the microsphere structure itself.

Any of a variety of therapeutics may be encapsulated in the liposomes. By therapeutic, as used herein, it is meant an agent having beneficial effect on the patient. As used herein, the term therapeutic is synonymous with the term drug.

Examples of drugs that may be delivered with gas-filled liposomes may contain for drug delivery purposes, but by no means is limited to; hormone products such as, vasopressin and oxytocin and their derivatives, glucagon, and thyroid agents as iodine products and anti-thyroid agents; cardiovascular products as chelating agents and mercurial diuretics and cardiac glycosides; respiratory products as xanthine derivatives (theophylline & aminophylline); anti-infectives as aminoglycosides, antifungals (amphotericin), penicillin and cephalosporin antibiotics, antiviral agents as Zidovudine, Ribavirin, Amantadine, Vidarabine, and Acyclovir, anti-helmintics, antimalarials, and antituberculous drugs; biologicals as immune serums, antitoxins and antivenins, rabies prophylaxis products, bacterial vaccines, viral vaccines, toxoids; antineoplastics as nitrosureas, nitrogen mustards, antimetabolites (fluorouracil, hormones as progesings and estrogens and antiestrogens; antibiotics as Dactinomycin; mitotic inhibitors as Etoposide and the Vinca alkaloids, Radiopharmaceuticals as radioactive iodine and phosphorus products; as well as Interferon, hydroxyurea, procarbazine, Dacarbazine, Mitotane, Asparaginase and cyclosporins.

Genetic and bioactive materials may be incorporated into the internal gas-filled space of these liposomes during the gas installation process or into or onto the lipid membranes of these particles. Incorporation onto the surface of these particles is preferred. Genetic materials and bioactive products with a high octanol/water partition coefficient may be incorporated directly into the lipid layer surrounding the gas but incorporation onto the surface of the gas-filled lipid spheres is more preferred. To accomplish this, groups capable of binding genetic materials or bioactive materials are generally incorporated into the lipid layers which will then bind these materials. In the case of genetic materials (DNA, RNA, both single stranded and double stranded and anti-sense and sense oligonucleotides) this is readily accomplished through the use of cationic lipids or cationic polymers which may be incorporated into the dried lipid starting materials.

Other suitable therapeutics include, but are not limited to: antineoplastic agents, such as platinum compounds (e.g., spiroplatin, cisplatin, and carboplatin), methotrexate, adriamycin, taxol, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, and arabinosyl; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, and β-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fludrocortisone acetate; vitamins such as cyanocobalamin neinoic acid, retinoids and derivatives such as retinol palmitate, and α-tocopherol; peptides, such as manganese super oxide dimutase; enzymes such as alkaline phosphatase; anti-allergic agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), ribavirin and vidarabine monohydrate (adenine arabinoside, ara-A); antianginals such as diltiazem, nifedipine, verapamil, erythrityl tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; antiinflammatories such as difunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium.

In certain preferred embodiments, the therapeutic is a monoclonal antibody, such as a monoclonal antibody capable of binding to melanoma antigen.

Other preferred therapeutics include genetic material such as nucleic acids, RNA, and DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs), and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with proteins or other polymers.

Examples of genetic therapeutics that may be applied using the liposomes of the present invention include DNA encoding at least a portion of an HLA gene, DNA encoding at least a portion of dystroph:[n, DNA encoding at least a portion of CFTR, DNA encoding at least a portion of IL-2, DNA encoding at least a portion of TNF, an antisense oligonucleotide capable of binding the DNA encoding at least a portion of Ras.

DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, *Science* 258, 744–746.

If desired, more than one therapeutic may be applied using the liposomes. For example, a single liposome may contain more than one therapeutic or liposomes containing different therapeutics may be co-administered. By way of example, a monoclonal antibody capable of binding to melanoma antigen and an oligonucleotide encoding at least a portion of IL-2 may be administered at the same time. The phrase "at least a portion of," as used herein, means that the entire gene need not be represented by the oligonucleotide, so long as the portion of the gene :represented provides an effective block to gene expression.

Similarly, prodrugs may be encapsulated in the liposomes, and are included within the ambit of the term therapeutic, as used herein. Prodrugs are well known in the art and include inactive drug precursors which, when exposed to high temperature, metabolizing enzymes, cavitation and/or pressure, in the presence of oxygen or otherwise, or when released from the liposomes, will form active drugs. Such prodrugs can be activated in the method of the invention, upon the application of ultrasound to the prodrug-containing liposomes with the resultant cavitation, heating, pressure, and/or release from the liposomes. Suitable prodrugs will be apparent to those skilled in the art, and are described, for example, in Sinkula et al., *J. Pharm. Sci.* 1975 64, 181–210, the disclosure of which are hereby incorporated herein by reference in its entirety.

Prodrugs, for example,, may comprise inactive forms of the active drugs wherein a chemical group is present on the prodrug which renders it inactive and/or confers solubility or some other property to the drug. In this form, the prodrugs are generally inactive, but once the chemical group has been cleaved from the prodrug, by heat, cavitation, pressure, and/or by enzymes in the surrounding environment or otherwise, the active drug is generated. Such prodrugs are well described in the art, and comprise a wide variety of drugs bound to chemical groups through bonds such as esters to short, medium or long chain aliphatic carbonates, hemiesters of organic phosphate, pyrophosphate, sulfate, amides, amino acids, azo bonds, carbamate, phosphamide, glucosiduronate, N-acetylglucosamine and β-glucoside.

Examples of drugs with the parent molecule and the reversible modification or linkage are as follows: convallatoxin with ketals, hydantoin with alkyl esters, chlorphenesin with glycine or alanine esters, acetaminophen with caffeine complex, acetylsalicylic acid with THAM salt, acetylsalicylic acid with acetamidophenyl ester, naloxone with sulfate ester, 15-methylprostaglandin $F_{2\alpha}$ with methyl ester, procaine with polyethylene glycol, erythromycin with alkyl esters, clindamycin with alkyl esters or phosphate esters, tetracycline with betaine salts, 7-acylaminocephalosporins with ring-substituted acyloxybenzyl esters, nandrolone with phenylproprionate decanoate esters, estradiol with enol ether acetal, methylprednisolone with acetate esters, testosterone with n-acetylglucosaminide glucosiduronate (trimethylsilyl) ether, cortisol or prednisolone or dexamethasone with 21-phosphate esters.

Prodrugs may also be designed as reversible drug derivatives and utilized as modifiers to enhance drug transport to site-specific tissues. Examples of parent molecules with reversible modifications or linkages to influence transport to a site specific tissue and for enhanced therapeutic effect include isocyanate with haloalkyl nitrosurea, testosterone with propionate ester, methotrexate (3-5'-dichloromethotrexate) with dialkyl esters, cytosine arabinoside with 5'-acylate, nitrogen mustard (2,2'-dichloro-N-methyldiethylamine), nitrogen mustard with aminomethyl tetracycline, nitrogen mustard with cholesterol or estradiol or dehydroepiandrosterone esters and nitrogen mustard with azobenzene.

As one skilled in the art would recognize, a particular chemical group to modify a given drug may be selected to influence the partitioning of the drug into either the membrane or the internal space of the liposomes. The bond selected to link the chemical group to the drug may be selected to have the desired rate of metabolism, e.g., hydrolysis in the case of ester bonds in the presence of serum esterases after release from the gas-filled liposomes. Additionally, the particular chemical group may be selected to influence the biodistribution of the drug employed in the gas-filled drug carrying liposome invention, e.g., N,N-bis(2-chloroethyl)phosphorodiamidic acid with cyclic phosphoramide for ovarian adenocarcinoma.

Additionally, the prodrugs employed within the gas-filled liposomes may be designed to contain reversible derivatives which are utilized as modifiers of duration of activity to provide, prolong or depot action effects. For example, nicotinic acid may be modified with dextran and carboxymethyldextran esters, streptomycin with alginic acid salt, dihydrostreptomycin with pamoate salt, cytarabine (ara-C) with 5'-adamantoate ester, ara-adenosine (ara-A) with 5palmitate and 5'-benzoate esters, amphotericin B with methyl esters, testosterone with 17-β-alkyl esters, estradiol with formate ester, prostaglandin with 2-(4-imidazolyl)ethylamine salt, dopamine with amino acid amides, chloramphenicol with mono- and bis(trimethylsilyl) ethers, and cycloguanil with pamoate salt. In this form, a depot or reservoir of long-acting drug may be released in vivo from the gas-filled prodrug bearing liposomes.

In addition, compounds which are generally thermally labile may be utilized to create toxic free radical compounds. Compounds with azolinkages, peroxides and disulfide linkages which decompose with high temperature are preferred. With this form of prodrug, azo, peroxide or disulfide bond containing compounds are activated by cavitation and/or increased heating caused by the interaction of high energy sound with the gas-filled liposomes to create cascades of free radicals from these prodrugs entrapped therein. A wide variety of drugs or chemicals may constitute these prodrugs, such as azo compounds, the general structure of such compounds being R—N=N—R, wherein R is a hydrocarbon chain, where the double bond[between the two nitrogen atoms may react to create free radical products in vivo.

Exemplary drugs or compounds which may be used to create free radical products include azo containing compounds such as azobenzene, 2,2'-azobisisobutyronitrile, azodicarbonamide, azolitmin, azomycin, azosemide, azosulfamide, azoxybenzene, aztreonam, sudan III, sulfachrysoidine, sulfamidochrysoidine and sulfasalazine, compounds containing disulfide bonds such as sulbentine, thiamine disulfide, thiolutin, thiram, compounds containing peroxides such as hydrogen peroxide and benzoylperoxide, 2,2'-azobisisobutyronitrile, 2,2'-azobis(2-amidopropane) dihydrochloride, and 2,2'-azobis(2,4-dimethylvaleronitrile).

A gas-filled liposome filled with oxygen gas should create extensive free radicals with cavitation. Also, metal ions from the transition series, especially manganese, iron and copper can increase the rate of formation of reactive oxygen intermediates from oxygen. By encapsulating metal ions within the liposomes, the formation of free radicals in vivo can be increased. These metal ions may be incorporated into the liposomes as free salts, as complexes, e.g., with EDTA, DTPA, DOTA or desferrioxamine, or as oxides of the metal ions. Additionally, derivatized complexes of the metal ions may be bound to lipid head groups, or lipophilic complexes of the ions may be incorporated into a lipid bilayer, for example. When exposed to thermal stimulation, e.g., cavitation, these metal ions then will increase the rate of formation of reactive oxygen intermediates. Further, radiosensitizers such as metronidazole and misonidazole may be incorporated into the gas-filled liposomes to create free radicals on thermal stimulation.

By way of an example of the use of prodrugs, an acylated chemical group may be bound to a drug via an ester linkage which would readily cleave in vivo by enzymatic action in serum. The acylated prodrug is incorporated into the gas-filled liposome of the invention. When the gas-filled liposome is popped by the sonic pulse from the ultrasound, the prodrug encapsulated by the liposome will then be exposed to the serum. The ester linkage is then cleaved by esterases in the serum, thereby generating the drug.

Similarly, ultrasound may be utilized not only to rupture the gas-filled liposome, but also to cause thermal effects which may increase the rate of the chemical cleavage and the release of the active drug from the prodrug.

The liposomes may also be designed so that there is a symmetric or an asymmetric distribution of the drug both inside and outside of the liposome.

The particular chemical structure of the therapeutics may be selected or modified to achieve desired solubility such that the therapeutic may either be encapsulated within the internal gas-filled space of the liposome, attached to the liposome or enmeshed in the liposome. The surface-bound therapeutic may bear one or more acyl chains such that, when the bubble is popped or heated or ruptured via cavitation, the acylated therapeutic may then leave the surface and/or the therapeutic may be cleaved from the acyl chains chemical group. Similarly, other therapeutics may be formulated with a hydrophobic group which is aromatic or sterol in structure to incorporate into the surface of the liposome.

The present invention is further described in the following examples, which illustrate the preparation and testing of the gas-filled liposomes. The following examples should not be construed as limiting the scope of the appended claims.

EXAMPLES

Example 1

Preparation of Gas-filled Liposomes

Fifty mg of 1,2-Dipalmitoyl-Sn-Glycero-3-Phosphocholine (MW: 734.05, powder, Lot No. 160pc-183) (Avanti-Polar Lipids, Alabaster, Ala.) was weighed and hydrated with 5.0 ml of saline solution (0.9% NaCl) or phosphate buffered saline (0.8% sodium chloride, 0.02% potassium chloride, 0.115% dibasic sodium phosphate and 0.02% monobasic potassium phosphate, pH adjusted to 7.4) in a centrifuge tube. The hydrated suspension was then shaken on a vortex machine (Scientific Industries, Bohemia, N.Y.) for 10 minutes at an instrument setting of 6.5. A total volume of 12 ml was then noted. The saline solution decreased from 5.0 ml to about 4 ml.

The gas-filled liposomes made via this new method were then sized by optical microscopy. It was determined that the largest size of the liposomes ranged from about 50 to about 60 μm and the smallest size detected was about 8 μm. The average size ranged from about 15 to about 20 μm.

The gas-filled liposomes were then filtered through a 10 or 12 μm "NUCLEPORE" membrane using a Swin-Lok Filter Holder, (Nuclepore Filtration Products, Costar Corp., Cambridge, Mass.) and a 20 cc syringe (Becton Dickinsion & Co., Rutherford, N.J.). The membrane was a 10 or 12 μm "NUCLEPORE" membrane (Nuclepore Filtration Products, Costar Corp., Cambridge, Mass.). The 10.0 μm filter was placed in the Swin-Lok Filter Holder and the cap tightened down securely. The liposome solution was shaken up and it was transferred to the 20 cc syringe via an 18 gauge needle. Approximately 12 ml of liposome solution was placed into the syringe, and the syringe was screwed onto the Swin-Lok Filter Holder. The syringe and the filter holder assembly were inverted so that the larger of the gas-filled liposomes vesicles could rise to the top. Then the syringe was gently pushed up and the gas-filled liposomes were filtered in this manner.

The survival rate (the amount of the gas-filled liposomes that were retained after the extrusion process) of the gas-filled liposomes after the extrusion through the 10.0 μm filter was about 83–92%. Before hand extrusion, the volume of foam was about 12 ml and the volume of aqueous solution was about 4 ml. After hand extrusion, the volume of foam was about 10–11 ml and the volume of aqueous solution was about 4 ml.

The optical microscope was used again to determine the size distribution of the extruded gas-filled liposomes. It was determined that the largest size of the liposomes ranged from about 25 to about 30 μm and the smallest size detected was about 5 μm. The average size ranged from about 8 to about 15 μm.

It was found that after filtering, greater than 90% of the gas-filled liposomes were smaller than 15 μm.

Example 2

Preparation of Gas-filled Liposomes Incorporating Lyophilization

Fifty mg of 1,2-Dipalmitoyl-sn-Glycero-3-Phosphocholine, (MW: 734.05, powder) (Avanti-Polar Lipids, Alabaster, Ala.) was weighed and placed into a centrifuge tube. The lipid was then hydrated with 5.0 ml of saline solution (0.9% NaCl). The lipid was then vortexed for 10 minutes at an instrument setting of 6.5. After vortexing, the entire solution was frozen in liquid nitrogen. Then the sample was put on the lyophilizer for freeze drying. The sample was kept on the lyophilizer for 18 hours. The dried lipid was taken off the lyophilizer and rehydrated in 5 ml of saline solution and vortexed for ten minutes at a setting of 6.5. A small sample of this solution was pipetted onto a slide and the solution was viewed under a microscope. The size of the gas-filled liposomes was then determined. It was determined that the largest size of the liposomes was about 60 μm and the smallest size detected was about 20 μm. The average size ranged from about 30 to about 40 μm.

Example 3

Example of Gas-filled Liposome Preparation Above the Phase Transition Temperature of the Lipid Fifty mg of 1,2-Dipalmitoyl-Sn-Glycero-3-Phosphocholine (MW: 734.05, powder) (Avanti-Polar Lipids, Alabaster, Ala.) was weighed and placed into a centrifuge tube. Approximately two feet of latex tubing (0.25 in. inner diameter) was wrapped around[a conical centrifuge tube in a coil-like fashion. The latex tubing was then fastened down to the centrifuge tube with electrical tape. The latex tubing was then connected to a constant temperature circulation bath (VWR Scientific Model 1131). The temperature of the bath was set to 60° C. and the circulation of water was set to high speed to circulate through the tubing. A thermometer was placed in the lipid solution and found to be between 42° C. and 50° C.

The lipid solution was vortexed for a period of 10 minutes at a vortex instrument setting of 6.5. It was noted that very little foaming of the lipid (phase transition temp.=41° C.) did not appreciably form gas-filled liposomes. Optical microscopy revealed large lipidic particles in the solution. The number of gas-filled liposomes that formed at this temperature was less than 3% of the number that form at a temperature below the phase transition temperature. The solution was allowed to sit for 15 minutes until the solution temperature equilibrated to room temperature (25° C.). The solution was then vortexed for a duration of 10 minutes. After 10 minutes, it was noted that gas-filled liposomes formed.

Example 4

Preparation of Gas-filled Liposome Incorporating a Freeze-Thaw Procedure 50 mg of 1,2-Dipalmitoyl-Sn-Glycero-3-Phosphocholine (MW: 734.05, powder) (Avanti-Polar Lipids, Alabaster, Ala.) was weighed and placed into a centrifuge tube. The lipid was then hydrated with 5.0 ml of 0.9% NaCl added. The aqueous lipid solution was vortexed for 10 minutes at an instrument setting of 6.5. After vortexing, the entire solution was frozen in liquid nitrogen. The entire solution was then thawed in a water bath at room temperature (25° C.). The freeze thaw procedure was then repeated eight times. The hydrated suspension was then vortexed for 10 minutes at an instrument setting of 6.5. Gas-filled liposomes were then detected as described in Example 1.

Example 5

Preparation of Gas-filled Liposome with an Emulsifying Agent (Sodium Lauryl Sulfate)

Two centrifuge tubes were prepared, each having 50 mg of DPPC. 1 mol % (~0.2 mg of Duponol C lot No. 2832) of sodium lauryl sulfate was added to one of the centrifguge tubes, and the other tube received 10 mol % (2.0 mg of Duponol C lot No. 2832). Five ml of 0.9% NaCl was added to both centrifuge tubes. Both of the tubes were frozen in liquid nitrogen and lyophilized for approximately 16 hours. Both samples were removed from the lyophilizer and 5 ml of saline was added to both of the tubes. Both of the tubes were vortexed at position 6.5 for 10 minutes.

It was determined that the largest size of the gas-filled liposomes with 1 mol % of sodium lauryl sulfate was about 75 μm and the smallest size detected was about 6 μm. The average size ranged from about 15 to about 40 μm. It was determined that the .largest size of the gas-filled liposomes with 10 mol % of sodium lauryl sulfate was about 90 μm and the smallest size detected was about 6 μm. The average size ranged from about 15 to about 35 μm.

The volume of foam in the solution containing gas-filled liposomes with 1 mol % sodium lauryl sulfate was about 5 ml and the volume of aqueous solution was about 3–4 ml. The volume of foam in the solution containing gas-filled liposomes with 10 mol % sodium lauryl sulfate was also about 15 ml and the volume of aqueous solution was about 3–4 ml.

Example 6

Determination of Whether Gas-filled Loposomes Can be Generated by Sonication 50 mg of lipid, 1,2-Dipalmitoyl-Sn-Glycero-3-Phosphocholine (Avanti-Polar Lipids, Alabaster, Ala.), was weighed out and hydrated with 5 ml of 0.9% NaCl. Instead of vortexing, the aqueous solution was sonicated using a Heat Systems Sonicator Ultrasonic: Processor XL (Heat Systems, Inc., Farmingdale, N.Y.) Model XL 2020. The sonicator, with a frequency of 20 KHz, was set to continuous wave, at position 4 on the knob of the sonicator. A micro tip was used to sonicate for 10 minutes. Following sonication, the solution was viewed under an optical microscope. There was no evidence of gas-filled liposomes having been produced.

Next, the micro tip of the sonicator was removed and replaced with the end cap that was supplied with the sonicator. Another solution (50 mg of lipid per 5 ml of saline) was prepared and sonicated with this tip. After 10 minutes, the solution was viewed under the microscope. Again, there was no evidence of gas-filled liposomes.

Example 7

Determination of Concentration Effects on Gas-Filled Liposome Production

This example determined whether a lower concentration limit of the lipid would halt the production of gas-filled liposomes. Ten mg of 1,2-Dipalmitoyl-Sn-Glycero-3-Phosphocholine (Avanti-Polar Lipids, Alabaster, Ala.) was added to 10 ml of saline. The lipid/saline solution was vortexed at position 6.5 for 10 minutes. The solution was viewed under an optical microscope for sizing. It was determined that the largest size of the liposomes ranged from about 30 to about 45 µm and the smallest size detected was about 7 µm. The average size ranged from about 30 to about 45 µm.

It appeared that the gas-filled liposomes were more fragile as they appeared to burst more rapidly than previously shown. Thus, it appears that concentration of the lipid is a factor in the generation and stability of gas-filled liposomes.

Example 8

Cascade Filtration

Unfiltered gas-filled liposomes may be drawn into a 50 ml syringe and passed through a cascade of a "NUCLEPORE" 10 µm filter and 8 µm filter that are a minimum of 150 µm apart (FIGS. 3 and 4). Alternatively, for example, the sample may be filtered through a stack of 10 µm and 8 µm filters that are immediately adjacent to each other. Gas-filled liposomes were passed through the filters at such a pressure whereby the flow rate was 2.0 ml min$^{-1}$. The subsequently filtered gas-filled liposomes were then measured for yield of gas-filled lipid liposomes which resulted in a volume of 80–90% of the unfiltered volume.

The resulting gas-filled liposomes were sized by four different methods to determine their size and distribution. Sizing was performed on a Particle Sizing Systems Model 770 Optical Sizing unit, a Zeiss Axioplan optical microscope interfaced to image processing software manufactured by Universal Imaging, and a Coulter Counter (Coulter Electronics Limited, Luton, Beds., England). As can be seen in FIGS. 5 and 6, the size of the gas-filled liposomes were more uniformly distributed around 8–10 µm as compared to the unfiltered gas-filled liposomes. Thus, it can be seen that the filtered gas-filled liposomes are of much more uniform size.

Example 9

Preparation of Filtered DPPC Suspension 250 mg DPPC (dipalmitoylphosphatidylcholine) and 10 ml of 0.9% NaCl were added to a 50 ml Falcon centrifuge tube (Becton-Dickinson, Lincoln Park, N.J.) and maintained at an ambient temperature (approx. 20° C.). The suspension was then extruded through a 1 µm Nuclepore (Costar, Pleasanton, Calif.) polycarbonate membrane under nitrogen pressure. The resultant suspension was sized on a Particle Sizing Systems (Santa Barbara, Calif.) Model 370 laser light scattering sizer. All lipid particles were 1 µm or smaller in mean outside diameter.

In addition, the same amount of DPPC suspension was passed five times through a Microfluidics™ (Microfluidics Corporation, Newton, Mass.) microfluidizer at 18,000 p.s.i. The suspension, which became less murky, was sized on a Particle Sizing Systems (Santa Barbara, Calif.) Sub Micron Particle Sizer Model 370 laser light scattering sizer where it was found that the size was uniformly less than 1 µm. The particle size of microfluidized suspensions is known to remain stable up to six months.

Example 10

Preparation of Filtered DSPC Suspension 100 mg DSPC (distearoylphosphatidylcholine) and 10 ml of 0.9% NaCl were added to a 50 ml Falcon centrifuge tube (Becton-Dickinson, Lincoln Park, N.J.). The suspension was then extruded through a 1 µm "NUCLEPORE" (Costar, Pleasanton, Calif.) polycarbonate membrane under nitrogen pressure at 300–800 p.s.i. The resultant suspension was sized on a Particle Sizing Systems (Santa Barbara, Calif.) Sub Micron Particle Sizer Model 370 laser light scattering sizer. It was found that all particles were 1 µm or smaller in size.

In addition, the same amount of DPPC suspension was passed five times through a Microfluidics™ (Microfluidics Corporation, Newton, Mass.), microfluidizer at 18,000 p.s.i. The resultant suspension, which was less murky, was sized on a Sub Micron Particle Sizer Systems Model 370 laser light scattering sizer and it was found that the size was uniformly less than 1 µm.

Example 11

Sterilization of Filtered Lipid Suspensions by Autoclaving

The previously sized suspensions of DPPC and DSPC of Examples 9 and 10 were subjected to autoclaving for twenty minutes on a Barnstead Model C57835 autoclave (Barnstead/Thermolyne, Dubuque, Iowa). After equilibration to room temperature (approx 20° C.) the sterile suspension was used for gas installation.

Example 12

Gas Installation of Filtered, Autoclaved Lipids via Vortexing 10 ml of a solution of 1,2-dipalmitoylphosphatidylcholine at 25 mg/ml in 0.9% NaCl, which had previously been extruded through a 1 μm filter and autoclaved for twenty minutes, was added to a Falcon 50 ml centrifuge tube (Becton-Dickinson, Lincoln Park, N.J.). After equilibration of the lipid suspension to room temperature (approximately 20° C.), the liquid was vortexed on a VWR Genie- 2 (120 V, 0.5 amp, 60 Hz.) (Scientific Industries, Inc., Bohemia, N.Y.) for 10 minutes or until a time that the total volume of gas-filled liposomes was at least double or triple the volume of the original aqueous lipid solution. The solution at the bottom of the tube was almost totally devoid of anhydrous particulate lipid, and a large volume of foam containing gas-filled liposomes resulted. Thus, prior autoclaving does not affect the ability of the lipid suspension to form gas-filled liposomes. Autoclaving does not change the size of the liposomes, and it does not decrease the ability of the lipid suspensions to form gas-filled liposomes.

Example 13

Gas Installation of Filtered, Autoclaved Lipids via Shaking on Shaker Table 10 ml of a solution of 1,2-dipalmitoylphosphatidylcholine at 25 mg/ml in 0.9% NaCl, which had previously been extruded through a 1 μm filter and autoclaved for twenty minutes, was added to a Falcon 50 ml centrifuge tube (Becton-Dickinson, Lincoln Park, N.J.). After equilibration of the lipid suspension to room temperature (approximately 20° C.), the tube was then placed upright on a VWR Scientific Orbital shaker (VWR Scientific, Cerritos, Calif.) and shaken at 300 r.p.m. for 30 minutes. The resultant agitation on the shaker table resulted in the production of gas-filled liposomes.

Example 14

Gas Installation of Filtered, Autoclaved Lipids via Shaking on Shaker Table via Shaking on Paint Mixer 10 ml of a solution of 1,2-dipalmitoylphosphatidylcholine at 25 mg/ml in 0.9% NaCl, which had previously been extruded through a 1 μm filter and autoclaved for twenty minutes, was added to a Falcon 50 ml centrifuge tube (Becton-Dickinson, Lincoln Park, N.J.). After equilibration of the lipid suspension to room temperature (approximately 20° C.), the tube was immobilized inside a 1 gallon empty household paint container and subsequently placed in a mechanical paint mixer employing a gyrating motion for 15 minutes. After vigorous mixing, the centrifuge tube was removed, and it was noted that gas-filled liposomes had formed.

Example 15

Gas Installation of Filtered, Autoclaved Lipids via Shaking by Hand 10 ml of a solution of 1,2-dipalmitoylphosphatidylcholine at 25 mg/ml in 0.9% NaCl, which had previously been extruded through a 1 μm nuclepore filter and autoclaved for twenty minutes, was added to a Falcon 50 ml centrifuge tube (Becton-Dickinson, Lincoln Park, N.J.). After equilibration of the lipid suspension to room temperature (approximately 20° C.), the tube was shaken forcefully by hand for ten minutes. Upon ceasing agitation, gas-filled liposomes were formed.

Example 16

Sizing Filtration of Autoclaved Gas-Filled Liposomes via Cascade or Stacked Filters Gas-filled liposomes were produced from DPPC as described in Example 12. The resultant unfiltered liposomes were drawn into a 50 ml syringe and passed through a cascade filter system consisting of a "NUCLEPORE" (Costar, Pleasanton, Calif.) 10 μm filter followed by an 8 μm filter spaced a minimum of 150 μm apart. In addition, on a separate sample, a stacked 10 μm and 8 μm filtration assembly was used, with the two filters adjacent to one another. Gas-filled liposomes were passed through the filters at a pressure such that they were filtered a rate of 2.0 ml/min. The filtered gas-filled liposomes yielded a volume of 80–90% of the unfiltered volume.

The resultant gas-filled liposomes were sized by four different methods to determine their size distribution. Sizing was performed on a Particle Sizing Systems (Santa Barbara, Calif.) Model 770 Optical Sizing unit, and a Zeiss (Oberkochen, Germany) Axioplan optical microscope interfaced to image processing software (Universal Imaging, West Chester, Pa.) and a Coulter Counter (Coulter Electronics Limited, Luton, Beds., England). As illustrated in FIG. 8, the size of the gas-filled liposomes was more uniformly distributed around 8–10 μm as compared to the unfiltered gas-filled liposomes.

Various modifications of the invention in addition to those shown and described herein will be apparent to those skilled in the art from the foregoing description. Such modifications are also intended to fall within the scope of the appended claims.

What is claimed is:

1. A method for preparing gas-filled lipid microspheres comprising shaking an aqueous solution comprising a lipid in the presence of a gas at a temperature below the gel state to liquid crystalline state phase transition temperature of the lipid.

2. A method as in claim 1 wherein the shaking step comprises vortexing.

3. A method as in claim 1 further comprising filtering and heat sterilizing said aqueous lipid solution.

4. A method as in claim 1 further comprising extruding the microspheres through at least one filter of a selected pore size.

5. A method as in claim 4 wherein the pore size is about 10 μm or smaller.

6. A method as in claim 1 further comprising hydrating a dried lipid to form an aqueous solution comprising a lipid.

7. The method of claim 1 wherein said microsphere comprises a lipid selected from the group consisting of dipalmitoylphosphatidylcholine, dipalmitoylphosphatidylethanolamine, and a phosphatidic acid, and said microsphere further comprising polyethylene glycol.

8. The method of claim 1 wherein said lipid comprises at least one dipalmitoyl lipid.

9. The method of claim 1 wherein said lipid comprises dipalmitoylphosphatidylethanolamine and polyethylene glycol.

10. The method of claim 1 wherein said lipid comprises dipalmitoylphosphatidylcholine, phosphatidic acid, dipalmitoylphosphatidylethanolamine, and polyethylene glycol.

11. The method of claim 1 wherein said microsphere comprises a gas selected from the group consisting of a fluorine gas and a nitrogen gas.

12. The method of claim 1 wherein said microsphere comprises a gas which is a fluorine gas.

13. The method of claim 1 wherein said microsphere comprises a gas which is nitrogen.

14. The method of claim 1 wherein said microsphere comprises a gas selected from the group consisting of a fluorine gas and a nitrogen gas and a lipid selected from the group consisting of dipalmitoylphosphatidylcholine, dipalmitoylphosphatidylethanolamine, and a phosphatidic acid, and said microsphere further comprising polyethylene glycol.

15. The method of claim 1 wherein said microsphere comprises a gas selected from the group consisting of a fluorine gas and a nitrogen gas and a lipid comprising dipalmitoylphosphatidylcholine, phosphatidic acid, dipalmitoylphosphatidylethanolamine, and polyethylene glycol.

16. The method of claim 1 wherein said microsphere comprises a gas which is a fluorine gas and a lipid comprising dipalmitoylphosphatidylethanolamine and polyethylene glycol.

17. The method of claim 1 wherein said microsphere comprises 90% gas.

18. The method of claim 1 wherein said microsphere comprises a gas which is a fluorine gas and a lipid comprising dipalmitoylphosphatidylethanolamine and polyethylene glycol, said microsphere comprising 90% gas.

19. The method of claim 1 performed at a pressure above ambient pressure.

* * * * *

UNITED STATES PATENT AND TRADEMARK OFFICE
CERTIFICATE OF CORRECTION

PATENT NO. : 5,469,854

DATED : November 28, 1995

INVENTOR(S) : Evan C. Unger, Thomas A. Fritz, Terry Matsunaga, VarandaRajan Ramaswami, David Yellowhair and Guanli Wu It is certified that error appears in the above-indentified patent and that said Letters Patent is hereby corrected as shown below:

Column 1, line 8, change "NO." to --No.--.

Column 5, line 61, after "the" delete ":".

Column 9, line 27, after "gas-filled" delete "2[".

Column 18, line 32, after "invention" delete ":".

Column 23, line 52, after "of" delete "dystroph:[n" and insert therefor --dystrophin--.

Column 25, line 49, after "bond" delete "[".

Column 28, line 3, after "around" delete "[".

Column 29, line 10, change "Loposomes" to --Liposomes--.

Column 30, line 67, change "installation" to "instillation".

UNITED STATES PATENT AND TRADEMARK OFFICE
CERTIFICATE OF CORRECTION

PATENT NO. : 5,469,854
DATED : November 28, 1995
INVENTOR(S) : Evan C. Unger, Thomas A. Fritz, Terry Matsunaga, VarandaRajan Ramaswami, David Yellowhair and Guanli Wu It is certified that error appears in the above-indentified patent and that said Letters Patent is hereby corrected as shown below:

Column 31, line 2, change "Installation" to "Instillation".

Column 31, line 26, change "Installation" to "Instillation".

Column 31, line 42, change "Installation" to "Instillation".

Column 31, line 61, change "Installation" to "Instillation"

Signed and Sealed this

Fourth Day of June, 1996

Attest:

BRUCE LEHMAN

Attesting Officer    Commissioner of Patents and Trademarks